United States Patent
Cohn

(10) Patent No.: US 9,623,193 B2
(45) Date of Patent: Apr. 18, 2017

(54) SYRINGE ASSEMBLY WITH AUTOMATIC SAFETY SHIELD

(71) Applicant: Robert J. Cohn, Dallas, PA (US)

(72) Inventor: Robert J. Cohn, Dallas, PA (US)

( * ) Notice: Subject to any disclaimer, the term of this patent is extended or adjusted under 35 U.S.C. 154(b) by 0 days.

(21) Appl. No.: 14/613,919

(22) Filed: Feb. 4, 2015

(65) Prior Publication Data

US 2015/0148749 A1    May 28, 2015

Related U.S. Application Data

(63) Continuation-in-part of application No. 13/312,520, filed on Dec. 6, 2011, now abandoned.

(51) Int. Cl.
*A61M 5/32*    (2006.01)

(52) U.S. Cl.
CPC .......... *A61M 5/3257* (2013.01); *A61M 5/326* (2013.01); *A61M 5/3243* (2013.01); *A61M 2005/3261* (2013.01); *A61M 2005/3264* (2013.01)

(58) Field of Classification Search
CPC .. A61M 5/3271; A61M 5/3243; A61M 5/326; A61M 2005/3261; A61M 5/3245; A61M 5/3137; A61M 5/3257
USPC .......................... 604/110, 198, 263; 128/919
See application file for complete search history.

(56) References Cited

U.S. PATENT DOCUMENTS

| | | | | | |
|---|---|---|---|---|---|
| 4,631,057 | A | * | 12/1986 | Mitchell | A61M 5/3243 604/198 |
| 4,639,249 | A | * | 1/1987 | Larson | A61M 5/31 604/198 |
| 4,731,059 | A | * | 3/1988 | Wanderer | A61B 5/1405 600/577 |
| 4,743,233 | A | * | 5/1988 | Schneider | A61M 5/3243 604/192 |
| 4,743,234 | A | | 5/1988 | Leopoldi et al. | |
| 4,927,416 | A | * | 5/1990 | Tomkiel | A61M 5/315 604/198 |
| 4,957,490 | A | * | 9/1990 | Byrne | A61M 5/24 604/110 |
| 5,163,918 | A | * | 11/1992 | Righi | A61M 5/326 128/919 |
| 5,246,427 | A | * | 9/1993 | Sturman | A61M 5/3275 604/192 |

(Continued)

OTHER PUBLICATIONS

BO Hypodermic Product Catalog "The Basis of Selection of Your Medication Delivery Device Needs" (2006).
BO SafetyGlide (TM) Product Offerings (2004) D.

*Primary Examiner* — Bhisma Mehta
*Assistant Examiner* — Matthew A Engel
(74) *Attorney, Agent, or Firm* — Mitchell A. Smolow

(57) ABSTRACT

A safety shield for use with a hypodermic syringe device is disclosed. The safety shield is moveable relative to the syringe barrel between retracted position and a needle containing position. In the retracted position, the syringe device may be used to inject the needle into the patient. After the medication has been injected or as the needle is withdrawn from the patient, in its operative mode the shield automatically extends from its retracted position to a needle containing position to shield the point of the needle to prevent accidental sticks and without further input from the operator to render the syringe unusable after a single injection.

15 Claims, 35 Drawing Sheets

(56) References Cited

U.S. PATENT DOCUMENTS

| | | | | |
|---|---|---|---|---|
| 5,411,492 | A * | 5/1995 | Sturman | A61M 5/3269 128/919 |
| 5,658,254 | A * | 8/1997 | Reichenbach | A61M 5/3243 604/110 |
| 6,945,960 | B2 | 9/2005 | Barker et al. | |
| 7,004,929 | B2 * | 2/2006 | McWethy | A61M 5/326 604/110 |
| 7,429,256 | B2 * | 9/2008 | Chevallier | A61M 5/326 604/110 |
| 7,601,139 | B2 * | 10/2009 | Woehr | A61M 5/3273 110/198 |
| 7,666,164 | B2 | 2/2010 | Giambattista et al. | |
| 7,803,132 | B2 * | 9/2010 | Janek | A61M 5/3234 604/110 |
| 7,922,698 | B2 * | 4/2011 | Riesenberger | A61M 5/3273 604/110 |
| 7,963,949 | B2 * | 6/2011 | Chevallier | A61M 5/326 604/110 |
| 2004/0006314 | A1 * | 1/2004 | Campbell, Jr. | A61M 5/3234 604/218 |
| 2011/0046605 | A1 * | 2/2011 | Chevalier | A61M 5/326 604/506 |
| 2013/0030377 | A1 * | 1/2013 | Chevalier | A61M 5/326 604/198 |
| 2013/0144255 | A1 | 6/2013 | Cohn | |

* cited by examiner

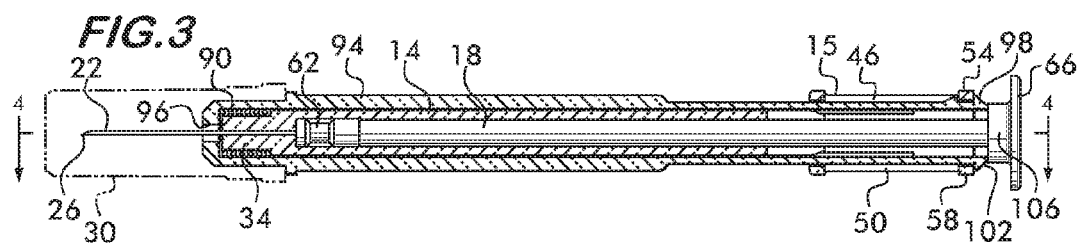
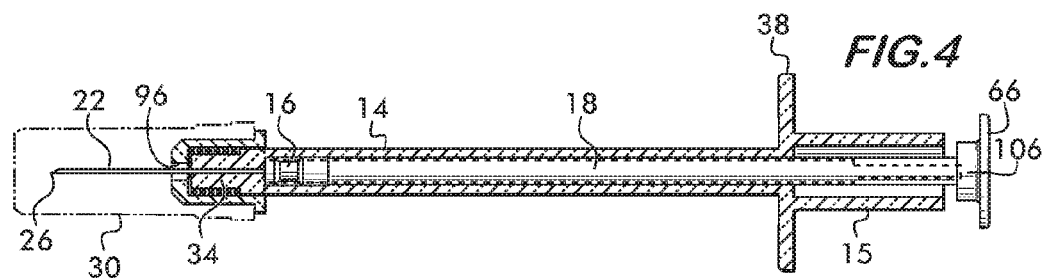

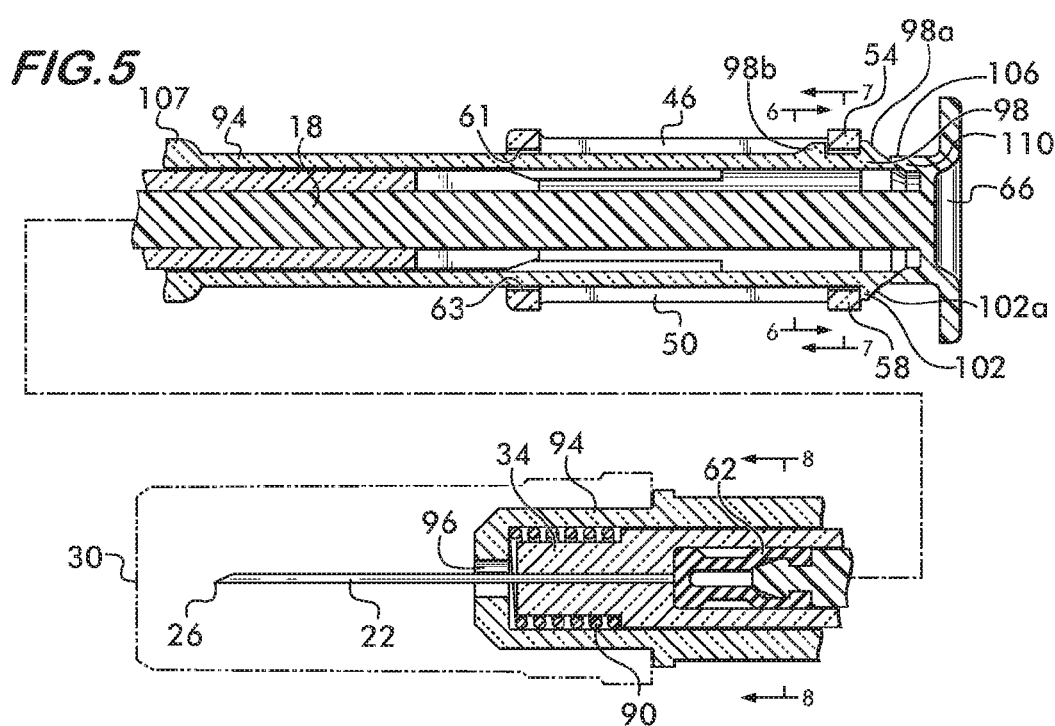

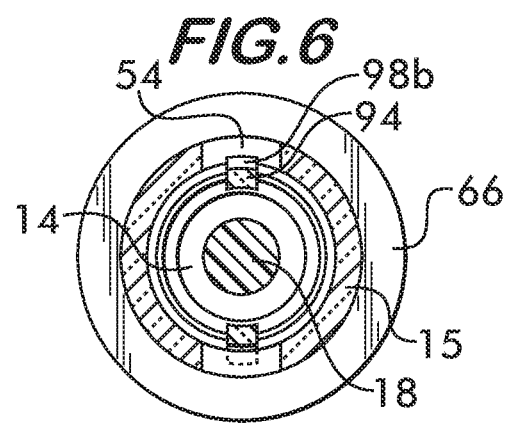
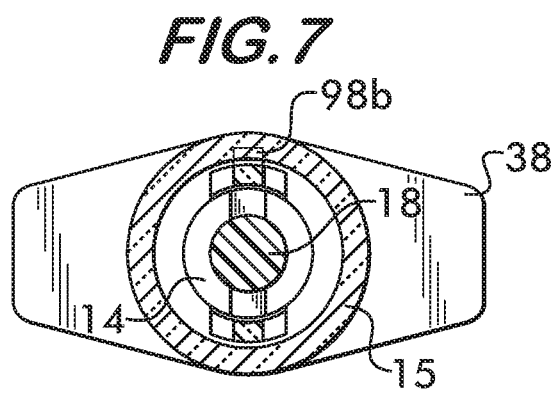
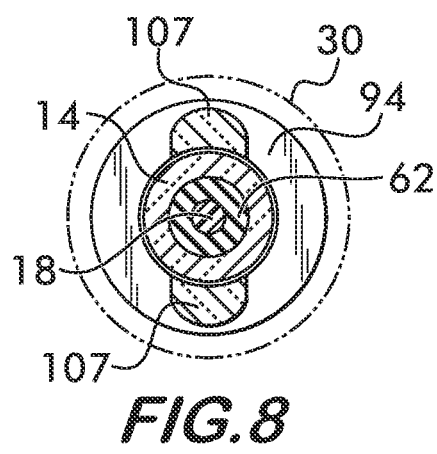

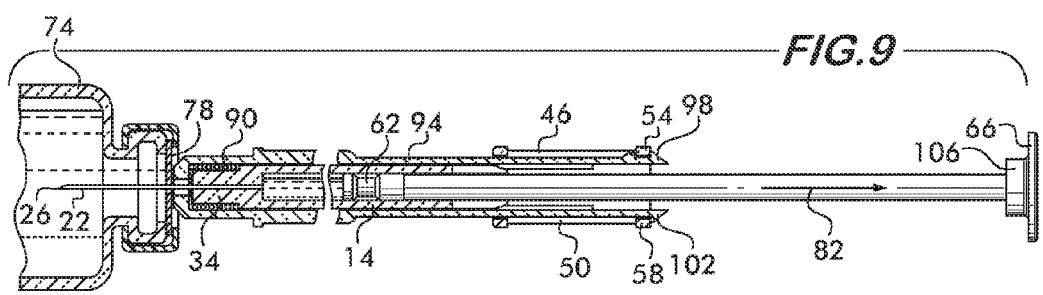
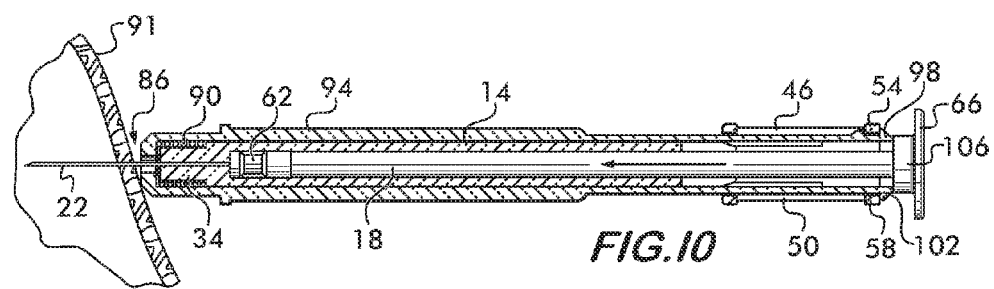

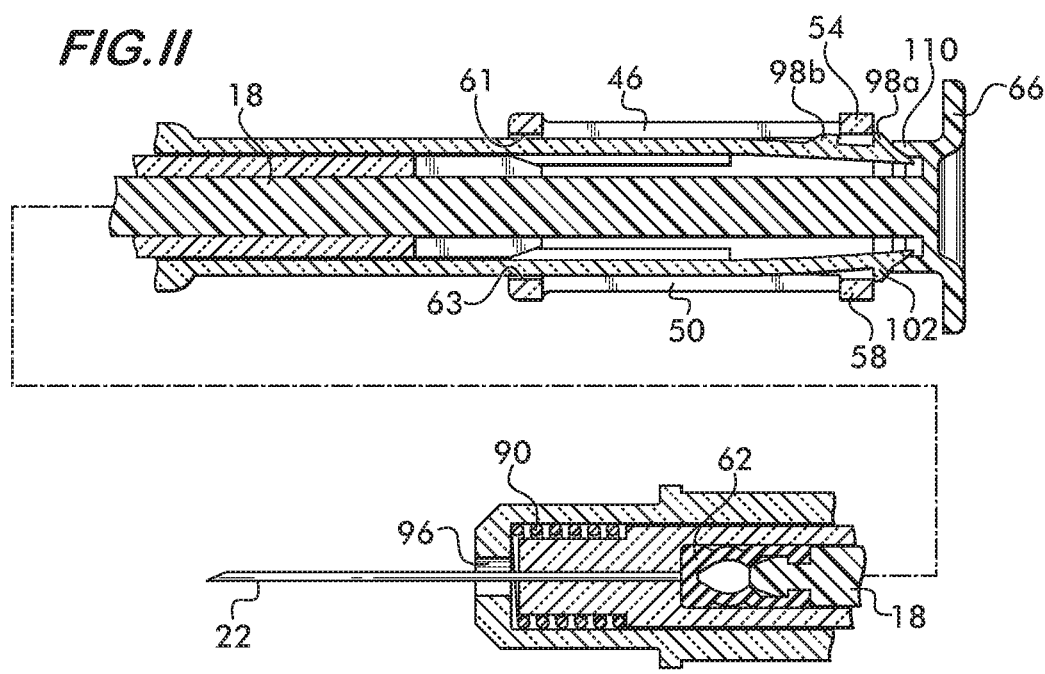

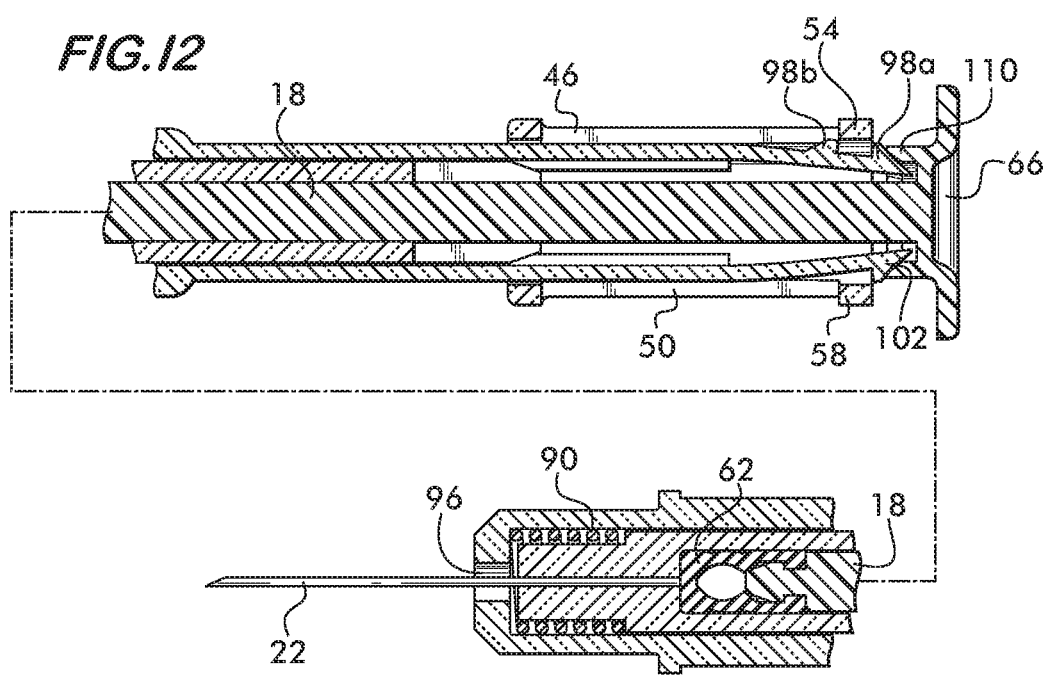

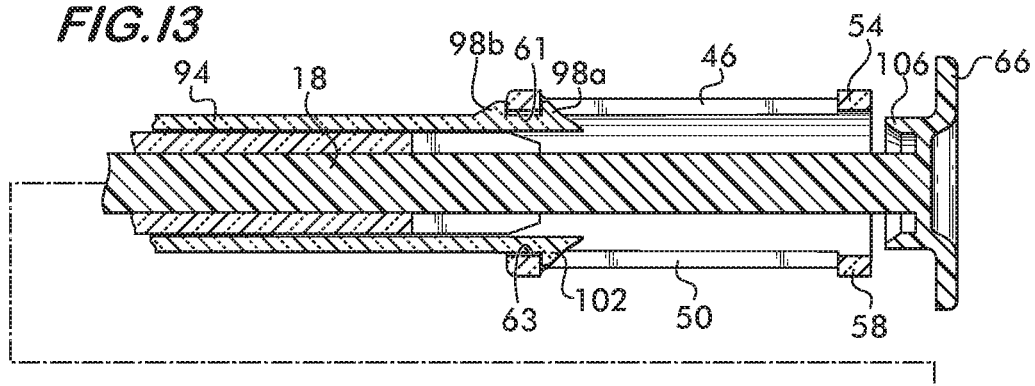
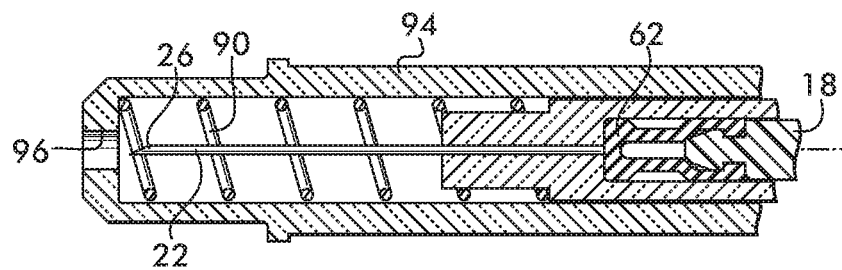
FIG.13

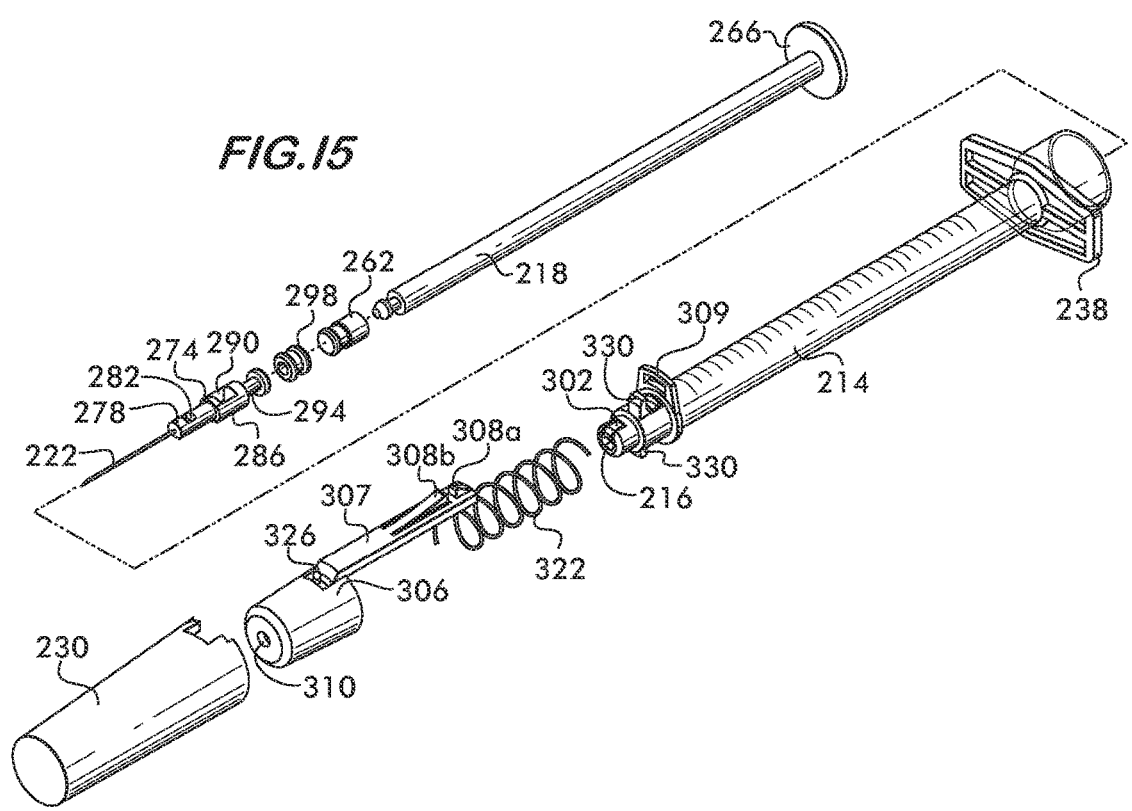

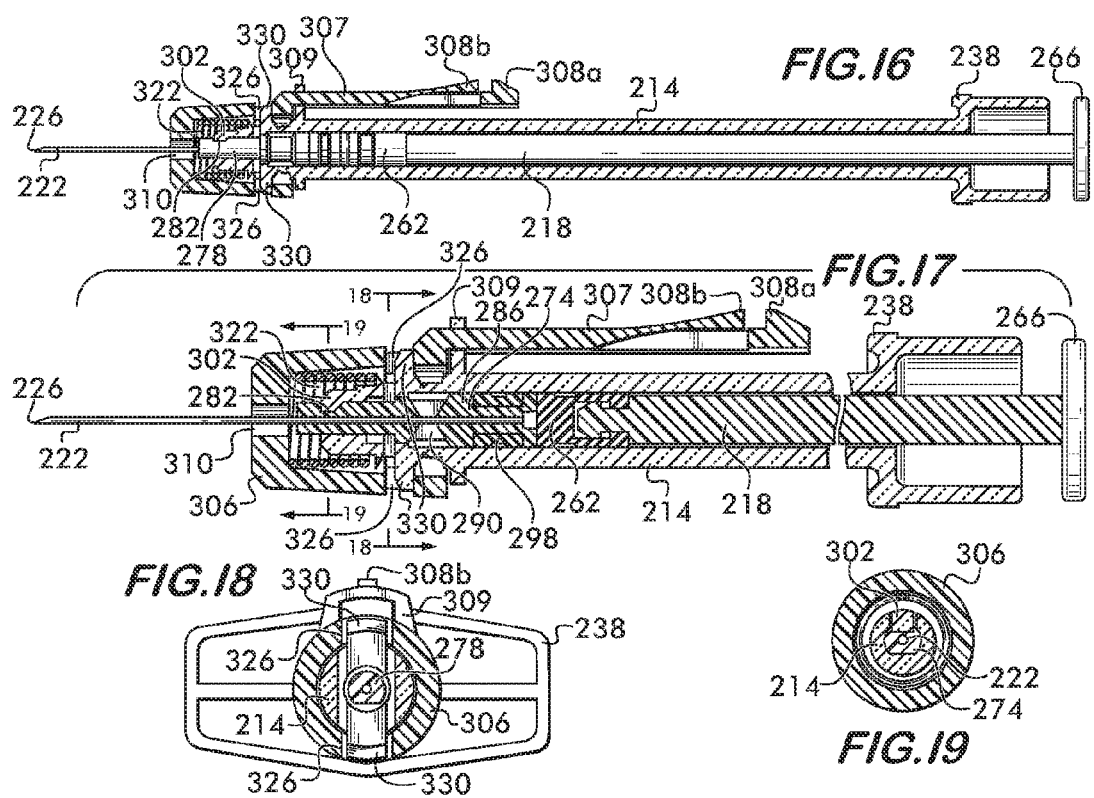

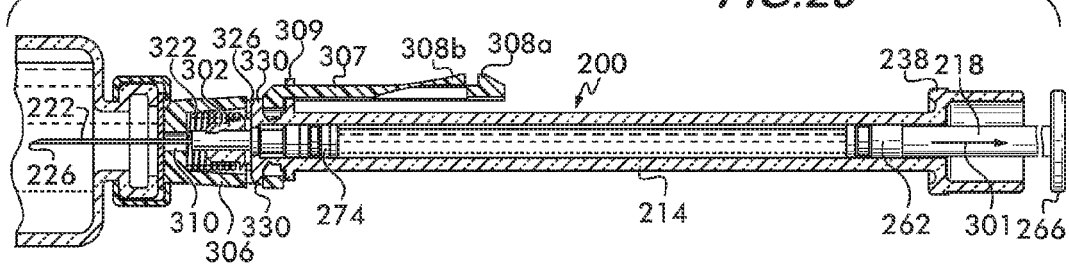
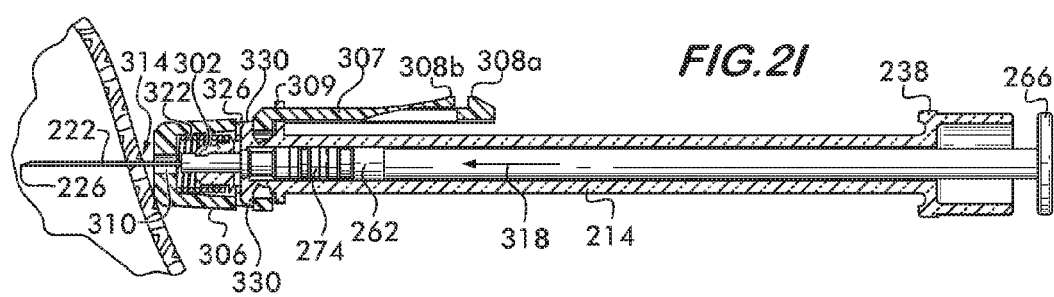

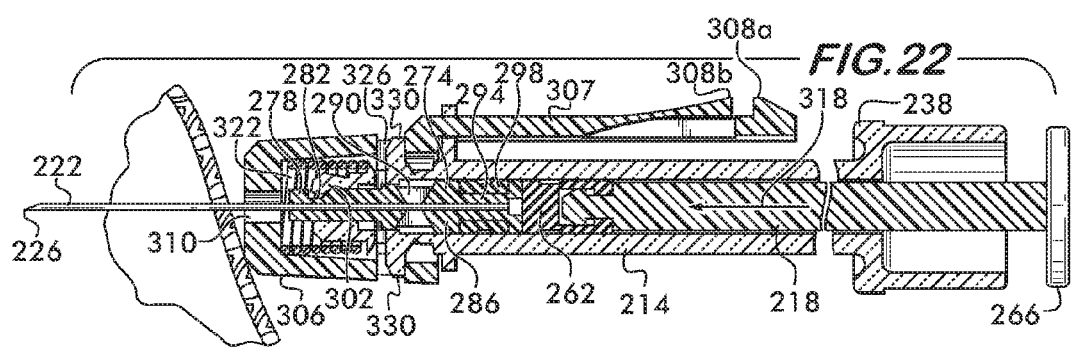
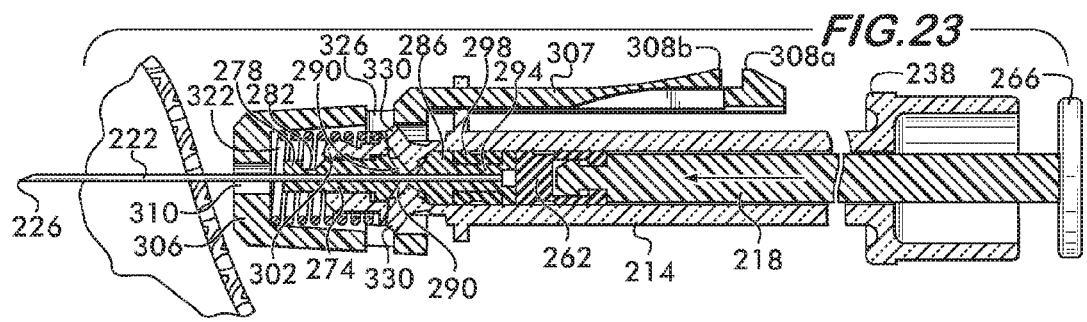

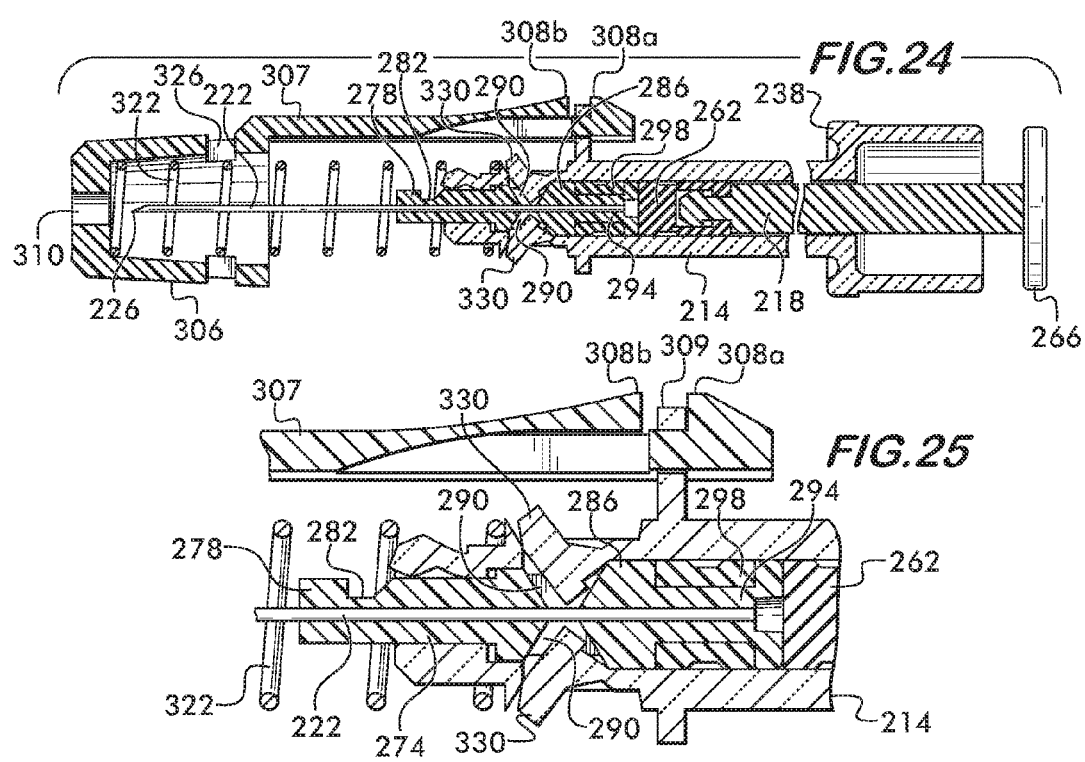

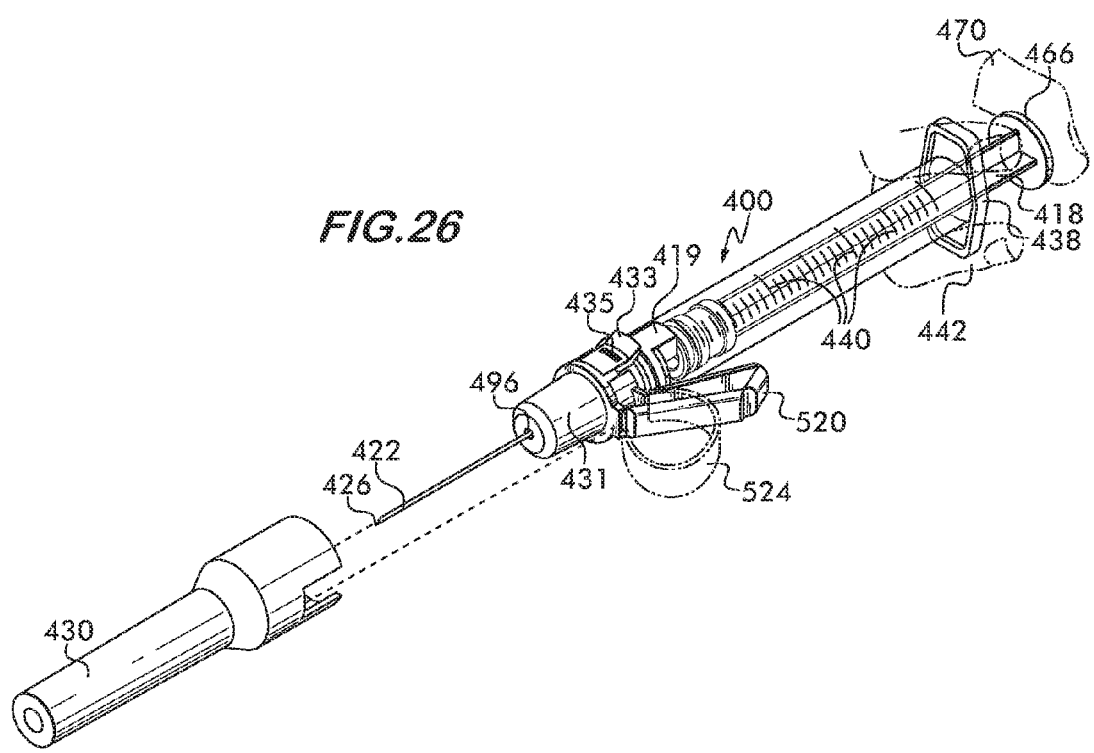

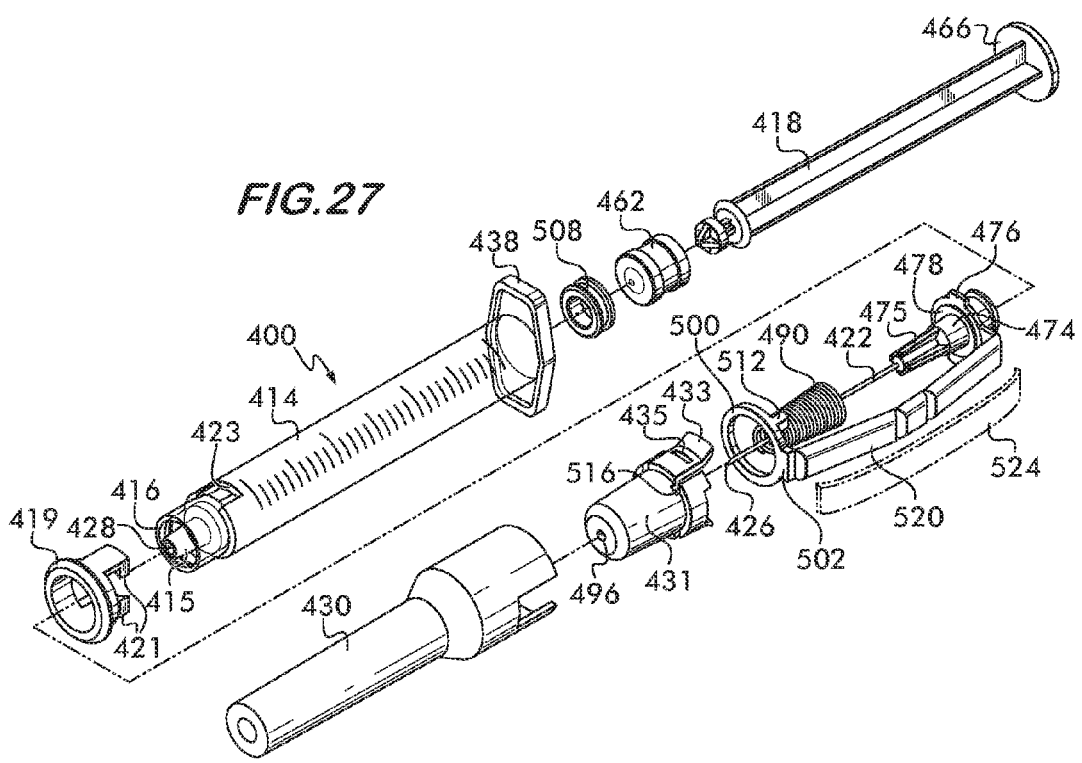

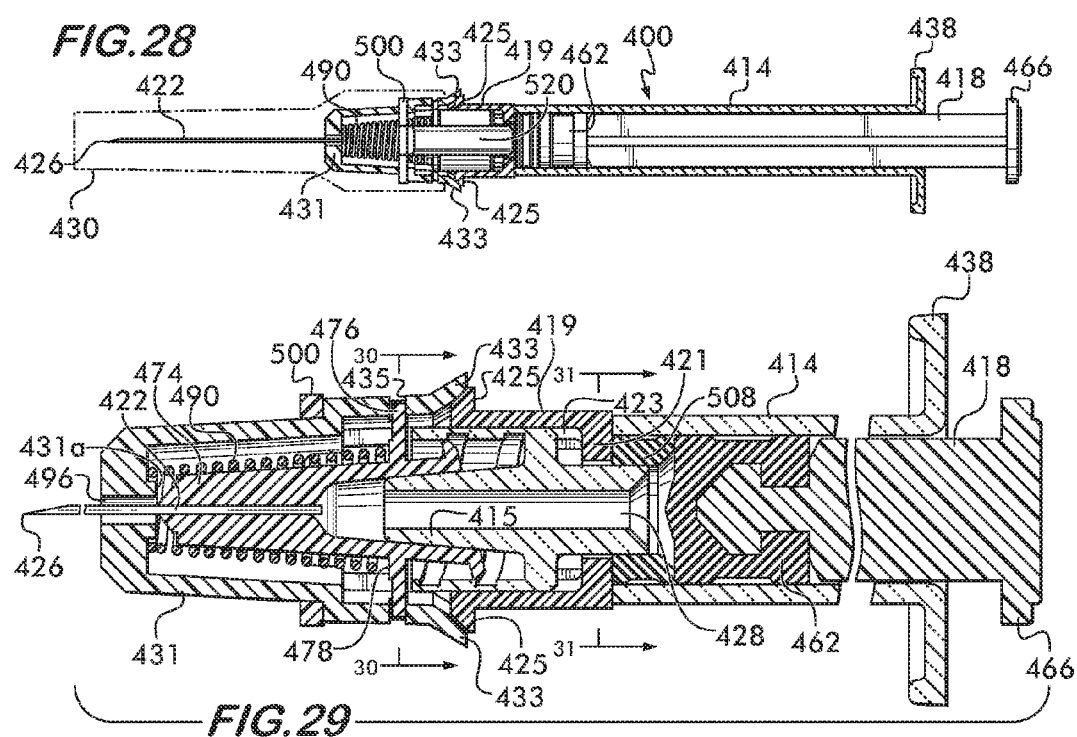

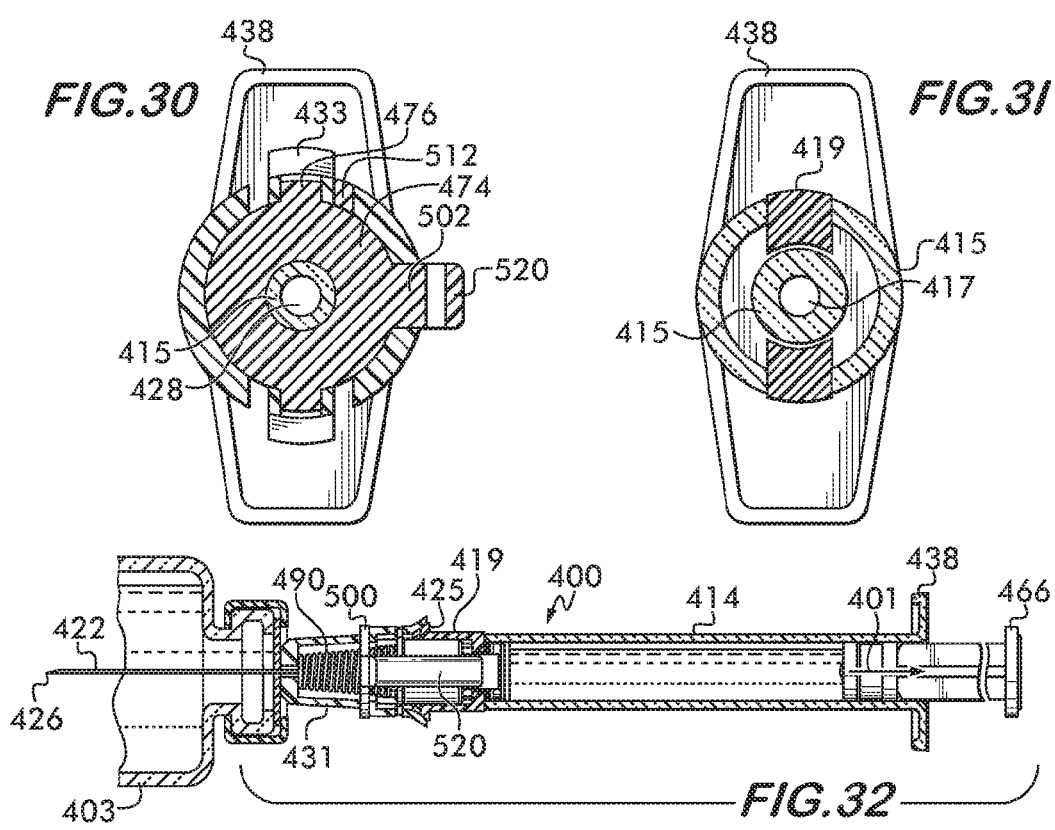

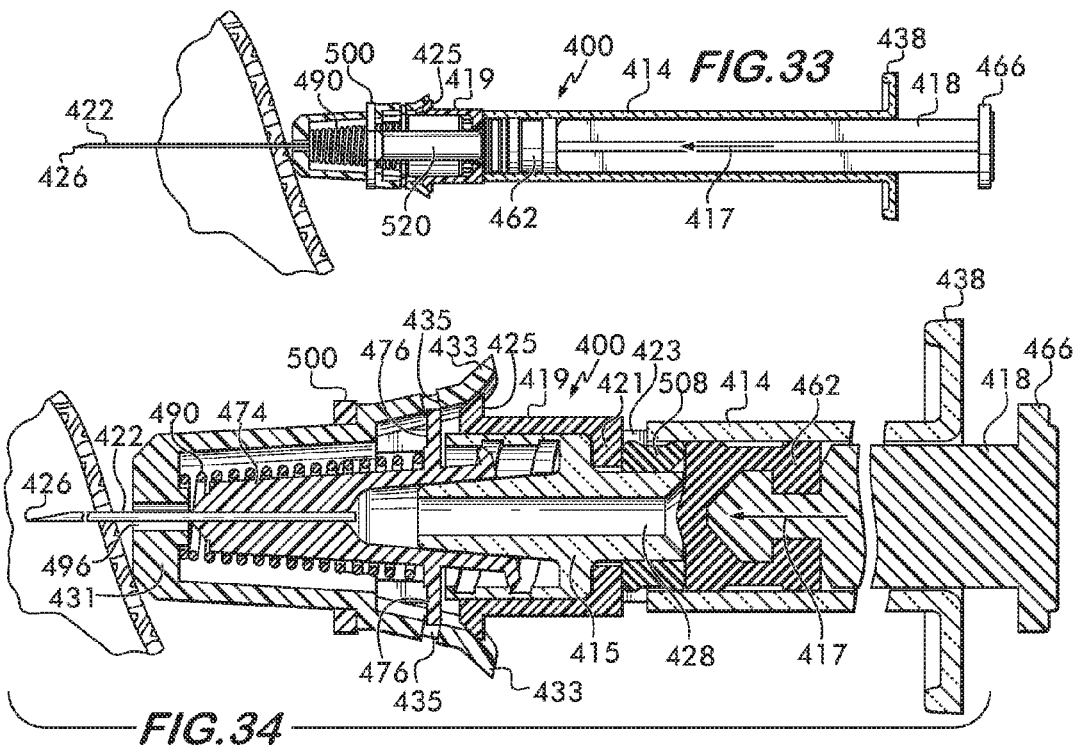

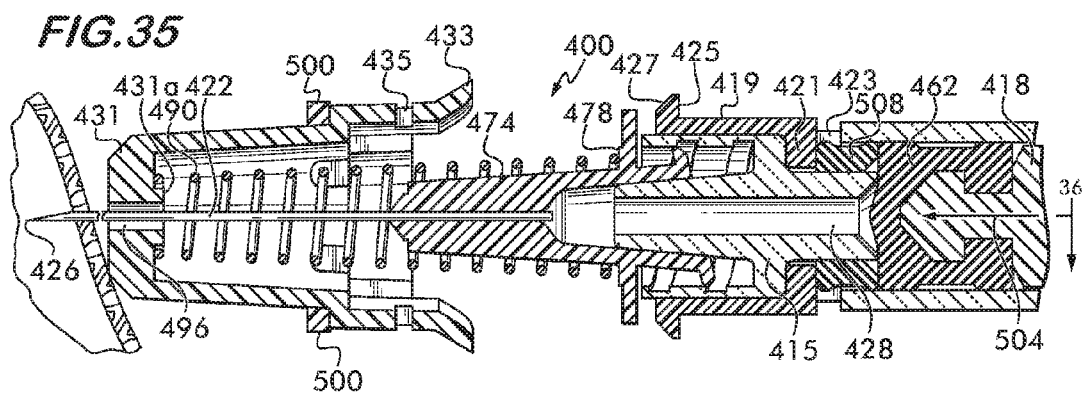
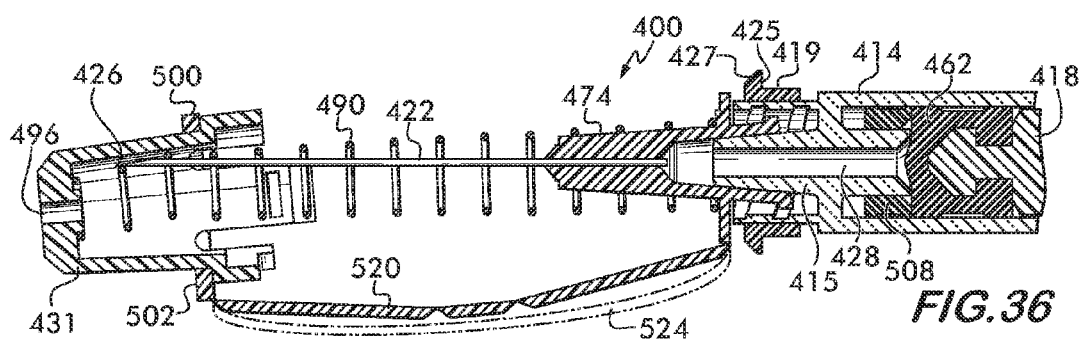

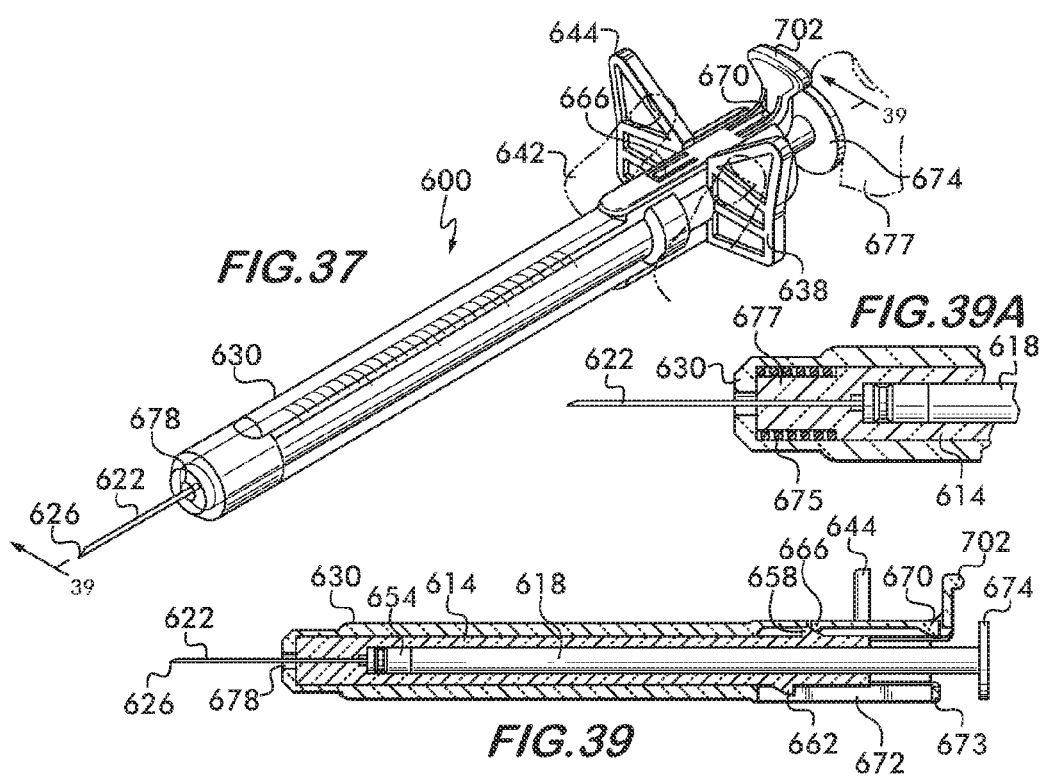

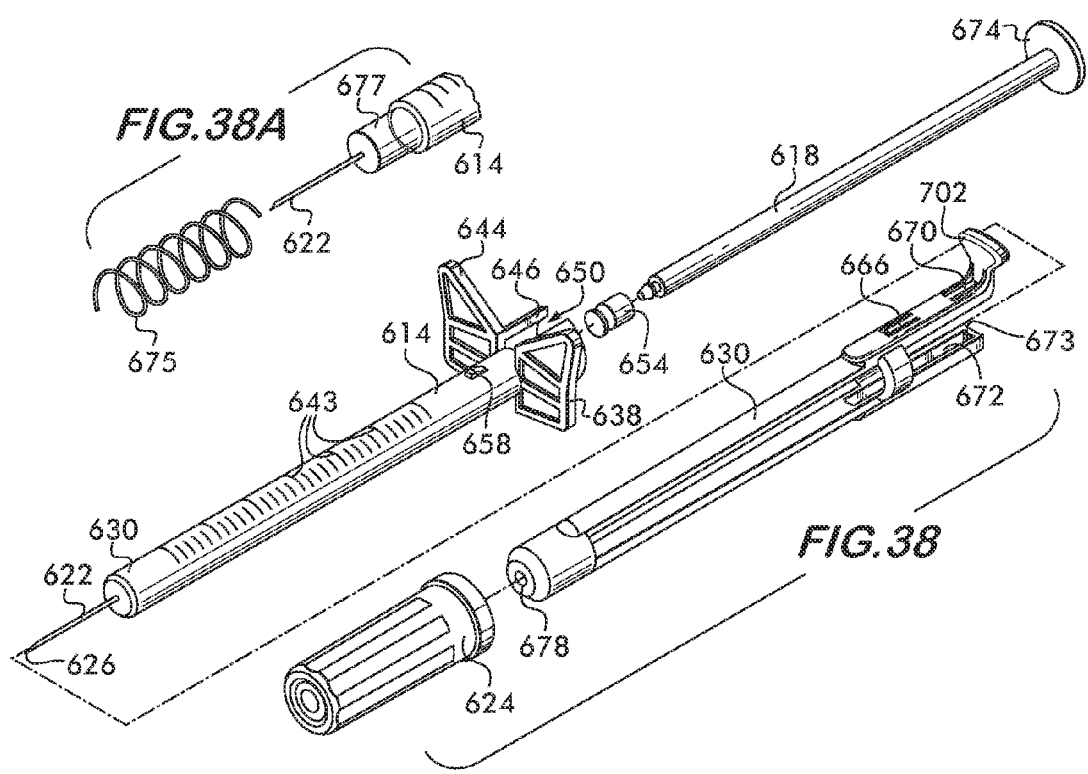

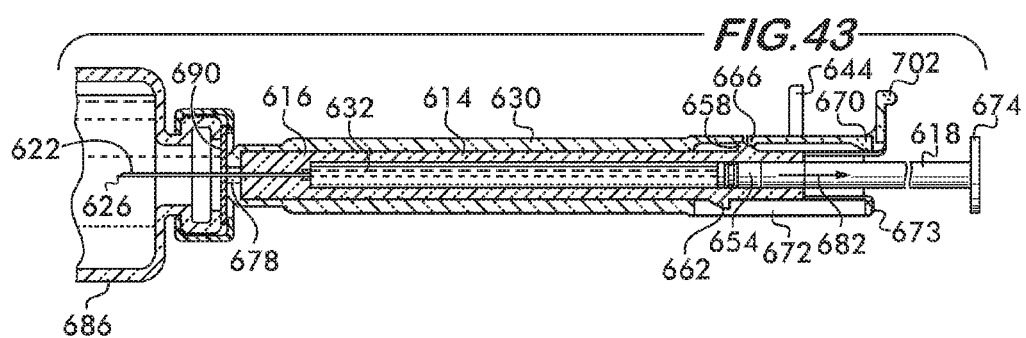
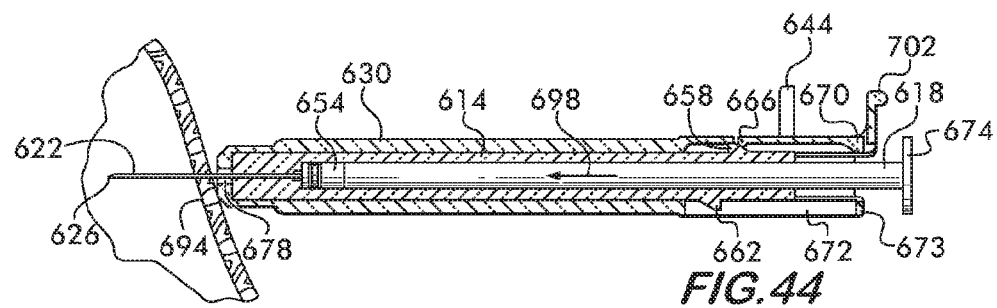

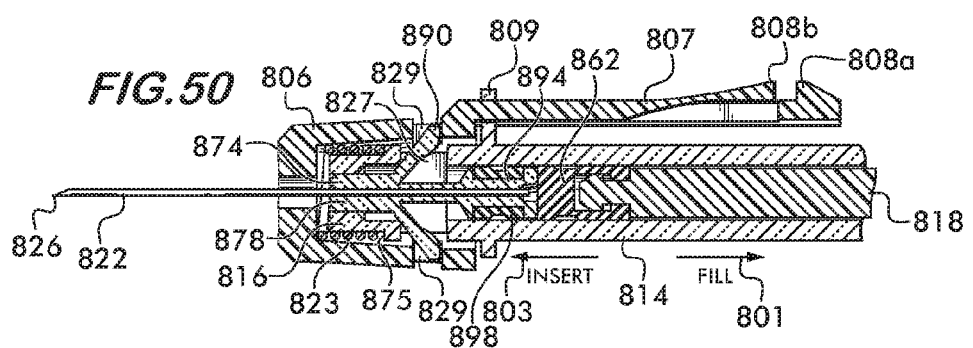
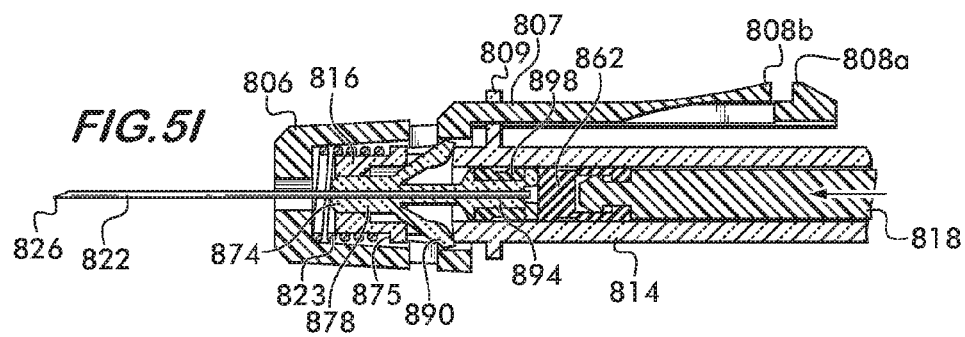

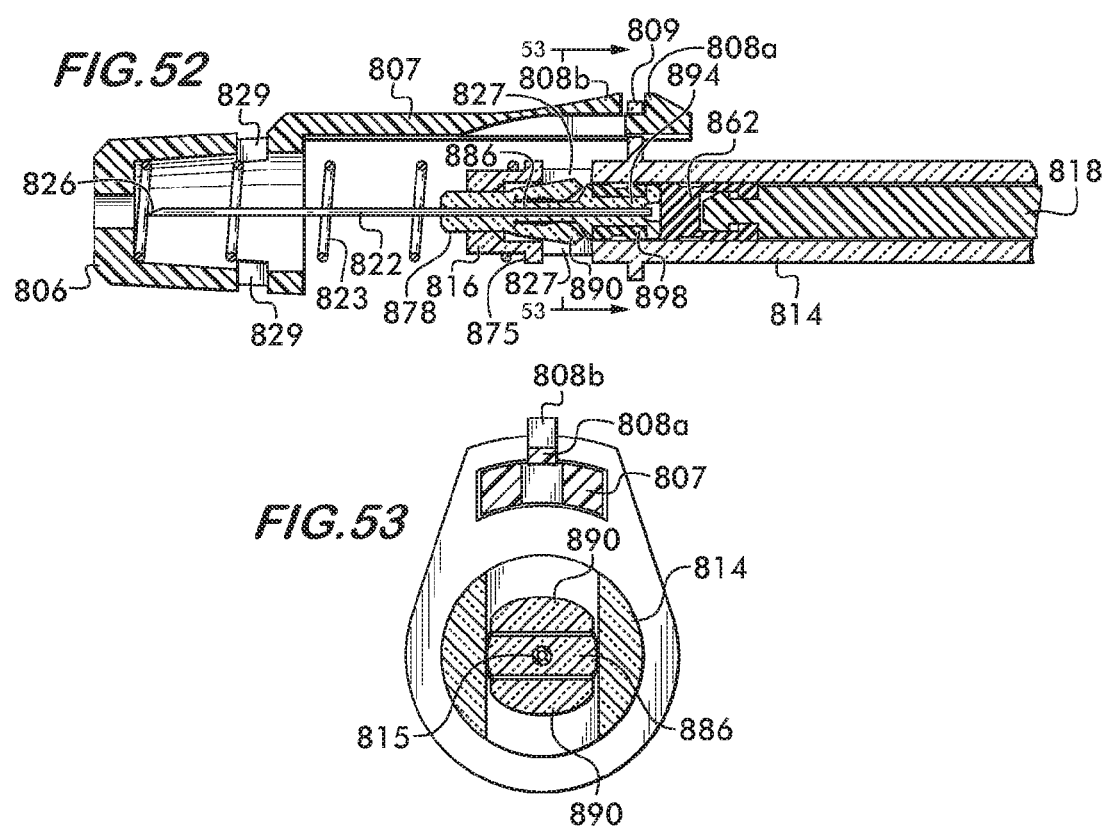

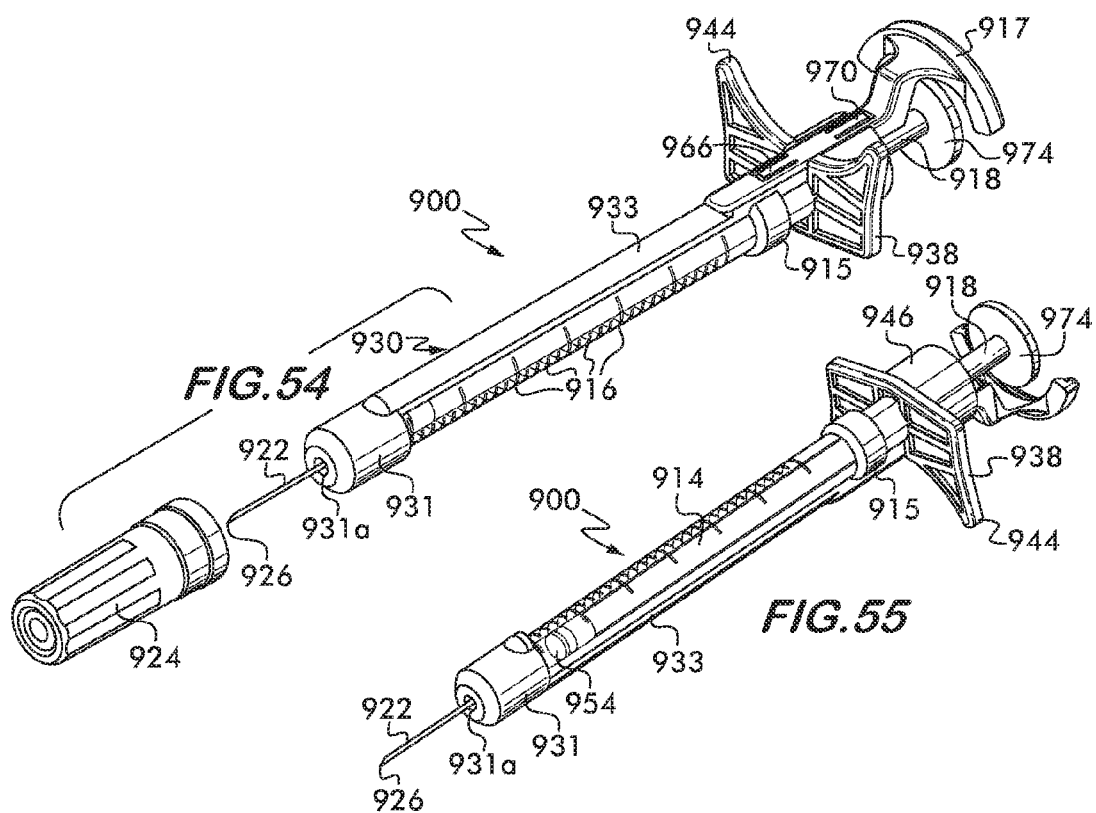

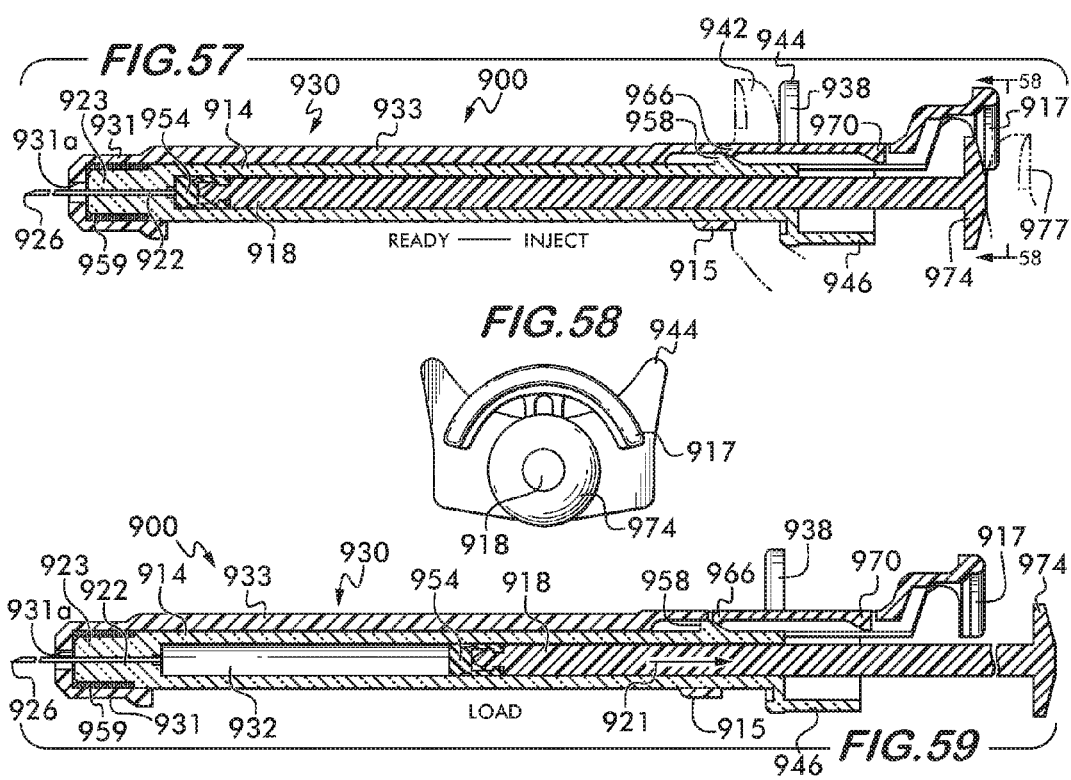

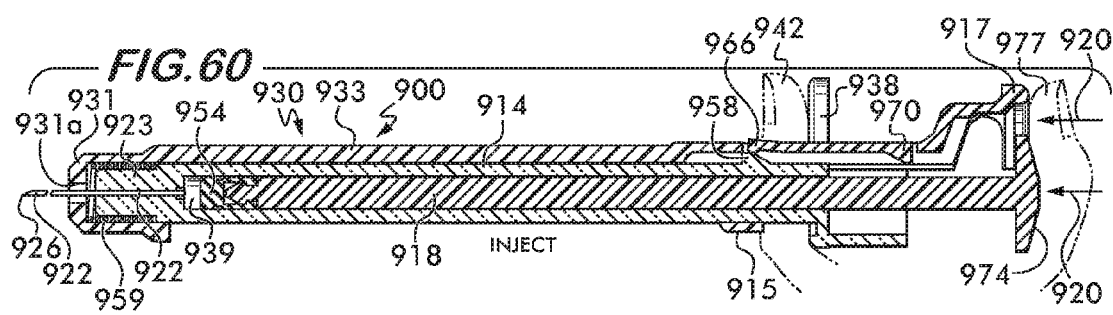
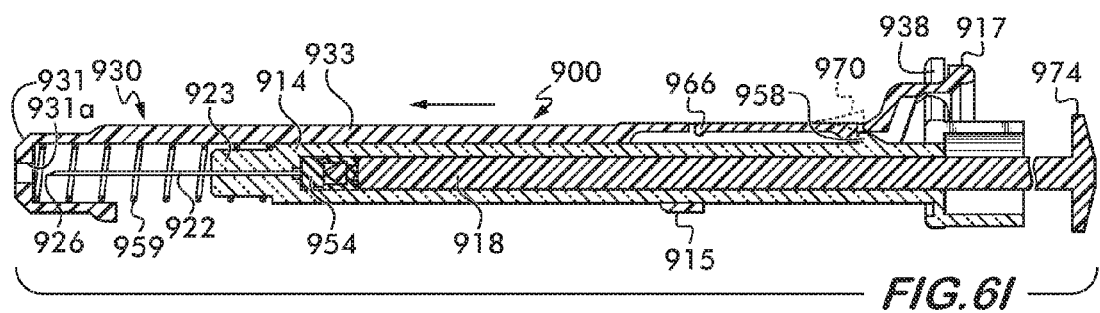

SYRINGE ASSEMBLY WITH AUTOMATIC SAFETY SHIELD

CROSS REFERENCE TO RELATED APPLICATIONS

This application is a continuation-in-part of and claims benefit of U.S. application Ser. No. 13/312,520 filed Dec. 6, 2011.

BACKGROUND OF THE INVENTION

Medical care of individuals requires the widespread use of needles for taking blood samples, intravenous drug delivery, and the introduction or removal of other fluids via cannula, needles, or syringes. In the current context, the use of hypodermic needles to deliver plasma, anesthetics, or other medications has become commonplace in medicine, science, veterinary medicine, and biotechnology. The use of a hypodermic needle typically involves first inserting a needle into the patient, injecting a substance or withdrawing a substance as required, and then removing the needle from the patient. In most applications, the withdrawn and contaminated needle must be handled very carefully during disposal to avoid needle stick injury.

To help prevent health care workers from becoming injured, guards have been developed to block the tip of these needles after use. Indeed, needle stick protection for medical professionals has become of particular importance in recent years because of the prevalence of potentially fatal infectious diseases, such as, for example, Acquired Immune Deficiency Syndrome (AIDS) and hepatitis, that can be transmitted by the exchange of bodily fluids through inadvertent wounds caused by accidental needle tip pricks after withdrawal from infected patients. Accordingly, many kinds of needle protection devices are available for providing post injection needle stick protection.

However, many of devices are cumbersome and interfere with a single-handed procedure, or require a conscious action by the operator to activate the needle shield, or require additional complicated pieces to attach a needle guard to the needle tip. Some needle guards require the user to reposition the hand to manually activate a second mechanism that then engages the needle guard, adding to the complexity of the design, manufacture and use of the hypodermic needle assembly. With other designs, it is possible for a user to accidentally insert a finger into the open distal end of the needle guard sleeve and thus come into contact with the contaminated needle tip. Other designs require that the user either slide or apply the needle shield to the tip of the needle by hand, significantly raising the risk of unintentional contact with the needle tip.

Accordingly, it is desirable to provide a device for injecting medication or withdrawing fluid wherein a contaminated needle is enclosed after use, which overcomes the aforementioned drawbacks. The needle enclosing device should be automatically activated immediately following the medication injection cycle requiring no further input from the operator.

BRIEF SUMMARY OF THE INVENTION

A safety shield for use with a hypodermic syringe device is disclosed. The safety shield is moveable relative to the syringe barrel between retracted position and a needle-containing position. In the retracted position, the syringe device may be used to inject the needle into the patient. After the medication has been injected or as the needle is withdrawn from the patient, in its operative mode the shield extends from its retracted position to a needle-containing position to shield the point of the needle to prevent accidental sticks and without further control from the operator to render the syringe unusable after a single injection.

BRIEF DESCRIPTION OF THE DRAWINGS

The invention will be described in conjunction with the following drawings in which like reference numerals designate like elements and wherein:

FIG. 3 is a cross-sectional view of the first embodiment of the present invention as it is provided to the medical professional in a packaged condition;

FIG. 4 is a cross-sectional view taken along line 4-4 of FIG. 3;

FIG. 5 is an enlarged cross-sectional view of the first embodiment of the present invention;

FIG. 6 is a cross-sectional view taken along line 6-6 of FIG. 5;

FIG. 7 is a cross-sectional view taken along line 7-7 of FIG. 5;

FIG. 8 is a cross-sectional view taken along line 8-8 of FIG. 5;

FIG. 9 is a cross-sectional view of the first embodiment of the present invention illustrating withdrawal of a liquid from a vial by withdrawing the plunger from the syringe barrel;

FIG. 10 is a cross-sectional view of the first embodiment of the present invention illustrating injection of a medicament at an injection site of a patient;

FIG. 11 is an enlarged cross-sectional view of the first embodiment of the present invention illustrating the manner for actuating and deploying the safety shield over the needle;

FIG. 12 is an enlarged cross-sectional view of the first embodiment of the present invention illustrating the manner for deploying the safety shield over the needle;

FIG. 13 is an enlarged cross-sectional view of the first embodiment of the present invention illustrating the safety shield deployed over the needle;

FIG. 15 is an exploded perspective view of the second embodiment of the present invention illustrating components of the embodiment;

FIG. 16 is a cross-sectional view of the second embodiment of the present invention illustrating the safety shield held in a retained position;

FIG. 17 is an enlarged cross-sectional view of the second embodiment of the present invention illustrating the safety shield held in the retained position;

FIG. 18 is a cross-sectional view taken along line 18-18 of FIG. 17;

FIG. 19 is a cross-sectional view taken along line 19-19 of FIG. 17;

FIG. 20 is a cross-sectional view of the second embodiment of the present invention illustrating withdrawal of a liquid from a vial by withdrawing the plunger from the syringe barrel;

FIG. 21 is a cross-sectional view of the second embodiment of the present invention illustrating injection of a medicament at an injection site of a patient;

FIG. 22 is a cross-sectional view of the second embodiment of the present invention illustrating the pivotable locking projection pivoting out of the needle-carrier during deployment of the outer shield over the needle;

FIG. 23 is a cross-sectional view of the second embodiment of the present invention illustrating opposed deformable members collapsing within opposed grooves of the needle-carrier during deployment of the outer shield over the needle;

FIG. 24 is a cross-sectional view of the second embodiment showing the outer shield in a deployed needle-containing position;

FIG. 25 is an enlarged cross-sectional view of a portion of the second embodiment showing the outer shield in the deployed needle-containing position;

FIG. 26 is a perspective view of a third embodiment of the present invention in the hand of a user;

FIG. 27 is an exploded perspective view of the third embodiment of the present invention illustrating the components of the embodiment;

FIG. 28 is a cross-sectional view of the third embodiment of the present invention;

FIG. 29 is an enlarged cross-sectional view of the third embodiment of the present invention;

FIG. 30 is a cross-sectional view taken along line 30-30 of FIG. 29;

FIG. 31 is a cross-sectional view taken along line 31-31 of FIG. 29;

FIG. 32 is a cross-sectional view of the third embodiment of the present invention illustrating withdrawal of a liquid medicament from a vial by withdrawing a plunger from the syringe barrel;

FIG. 33 is a cross-sectional view of the third embodiment of the present invention illustrating injection of a medicament at an injection site of a patient;

FIG. 34 is an enlarged cross-sectional view of the third embodiment of the present invention illustrating the manner for deploying the outer safety shield;

FIG. 35 is an enlarged cross-sectional view of the third embodiment of the present invention illustrating the outer shield being deployed towards an extended needle-containing position;

FIG. 36 is an enlarged cross-sectional view of the third embodiment of the present invention showing the outer shield deployed in the extended needle-containing position;

FIG. 37 is a perspective view of a fourth embodiment of the present invention;

FIG. 38 is an exploded perspective view of the fourth embodiment of the present invention illustrating the components of this embodiment;

FIG. 38A is an exploded perspective view of a portion of a spring-loaded alternative version of the fourth embodiment of the present invention;

FIG. 39 is a cross-sectional view of the fourth embodiment of the present invention showing the outer shield disposed in a retracted position;

FIG. 39A is a cross-sectional view of a portion of the spring-loaded alternative version of the fourth embodiment;

FIG. 43 is a cross-sectional view of the fourth embodiment of the present invention illustrating withdrawal of a liquid medicament from a vial by withdrawing the plunger from the syringe barrel;

FIG. 44 is a cross-sectional view of the fourth embodiment of the present invention illustrating injection of a medicament at an injection site of a patient;

FIG. 50 is an enlarged cross-sectional view of a portion of the fifth embodiment of the present invention illustrating the outer shield retained in a retracted position;

FIG. 51 is an enlarged cross-sectional view of a portion of the fifth embodiment of the present invention illustrating the outer shield retained in the retracted position;

FIG. 52 is an enlarged cross-sectional view of a portion of the fifth embodiment of the present invention illustrating the outer shield deployed in the needle-containing position;

FIG. 53 is a cross-sectional view taken along line 53-53 of FIG. 52;

FIG. 54 is a perspective view of a sixth embodiment of the present invention;

FIG. 55 is another perspective view of the sixth embodiment of the present invention;

FIG. 57 is an enlarged cross-sectional view of the sixth embodiment of the present invention illustrating the manner for deploying the outer shield shown retained in a retracted position;

FIG. 58 is a cross-sectional view taken along line 58-58 of FIG. 57;

FIG. 59 is an enlarged cross-sectional view of the sixth embodiment of the present invention illustrating a manner for drawing a fluid, e.g., a medicament, into the syringe barrel via a needle by retracting a plunger;

FIG. 60 is an enlarged cross-sectional view of the sixth embodiment of the present invention illustrating the manner for deploying the outer shield shown retained in a retracted position; and, FIG. 61 is an enlarged cross-sectional view of the sixth embodiment of the present invention illustrating the outer shield moved to the deployed needle-containing position.

DETAILED DESCRIPTION OF THE INVENTION

Figure 1:
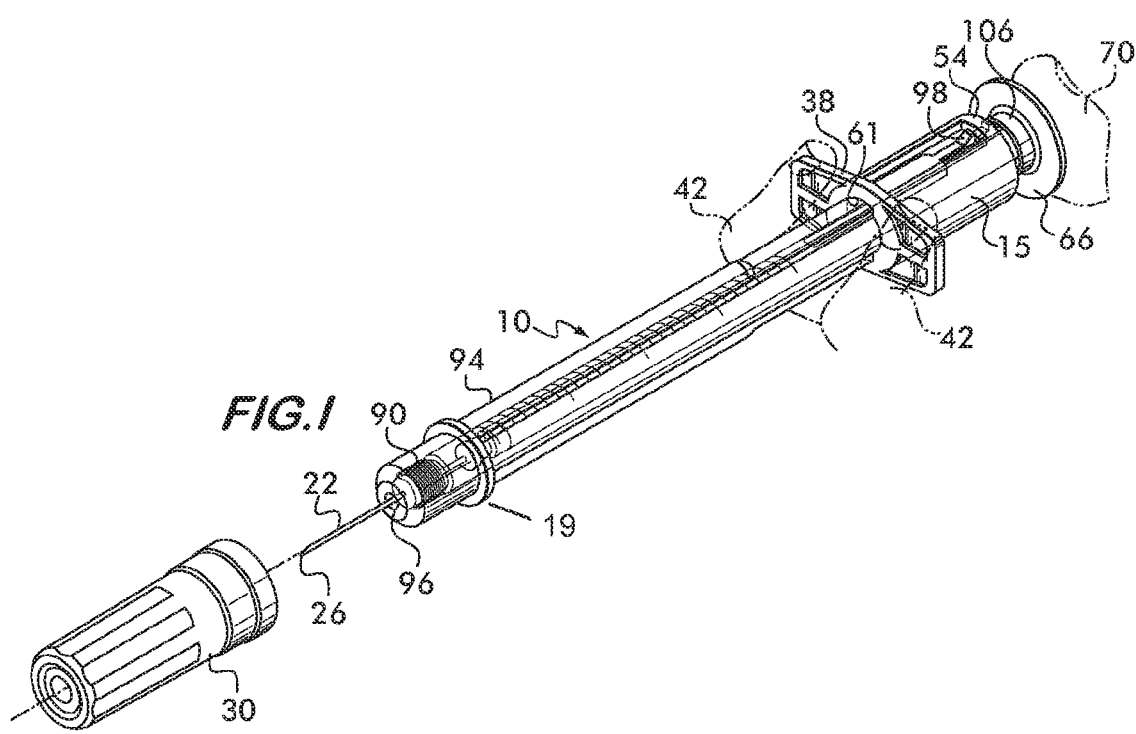
FIG. 1 is a perspective view of a first embodiment of the present invention.
Figure 2:
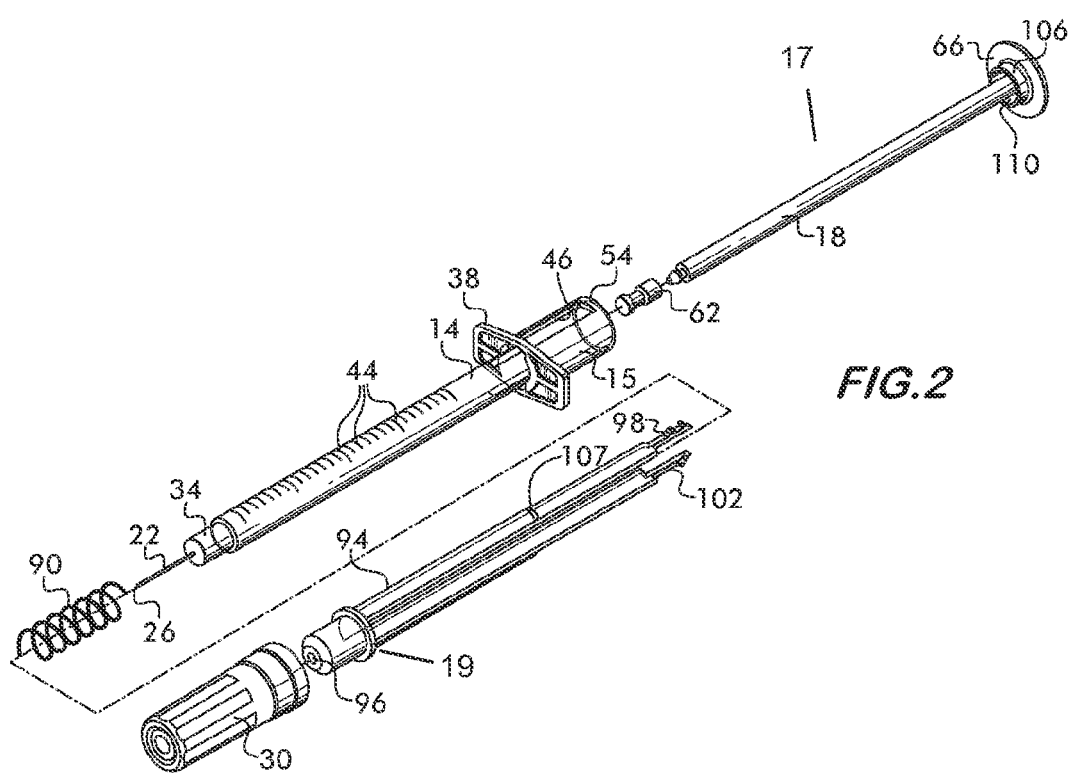
FIG. 2 is an exploded perspective view of the first embodiment of the present invention illustrating the components of the embodiment.

Referring now in detail to the various figures of the drawings wherein like reference characters refer to like parts, there is shown at 10 in FIGS. 1 through 4 a safety syringe assembly that includes a syringe barrel 14, a plunger 18, and a hypodermic needle 22 having a needle tip 26. The assembly 10 is arranged for use with a variety of commercially available needles. The assembly 10 also includes a needle protector cap 30 arranged to snap onto collar 19 at the distal end of the safety syringe assembly 10. The syringe barrel 14 is generally cylindrical and includes a forward end having a reduced diameter nozzle 34 (FIG. 2) adapted to receive the needle 22. The syringe barrel 14 defines a reservoir within which a fluid, e.g., a medicament, may be contained. The needle 22 or needle cannula (those terms being used interchangeably herein) extends axially and in the forward direction from the syringe barrel 14 and includes a forward tip 26. The needle 22 is in fluid communication with the reservoir through the reduced diameter nozzle 34 (FIG. 2). The syringe barrel 14 is preferably formed of a transparent or translucent molded plastic such as polyethylene, polypropylene, or polycarbonate.

The barrel 14 has an outwardly extending flange 38 located towards a proximal end thereof which facilitates gripping of the syringe barrel 14 with the user's fingers 42 (FIG. 1) when it is desired to move the plunger 18 relative to the barrel 14 linearly for normal use, such as when moving the plunger through an injection stroke to inject a fluid, e.g., a medicament into a patient. The finger flange 38 may be annular or oblong. The portion of the syringe barrel 14 forward of the finger flange 38 is substantially transparent and includes volume measuring indicia 44 (FIG. 2) on the surface thereof to enable a user to determine the volume of fluid within the barrel 14. For example, the syringe barrel 14 may hold up to 3.0 ml in volume, however, may hold other volumes greater or lesser.

Referring now to FIGS. 2, 4 and 5, a portion 15 of the syringe barrel 14 extends rearward from the finger flange 38 and is slightly larger in diameter than the forward portion and includes a pair of opposed elongated slots 46, 50 each bounded by a peripheral wall. Each peripheral wall of the slots 46, 50 includes an end wall 54, 58 located at the rear end of the syringe barrel 14. Each end wall 54, 58 serves as a first catch member, for example, a syringe barrel catch member, to retain an outer shield 94 in a retracted position wherein the needle 22 is exposed for use. In one embodiment a second catch member is located on the syringe barrel distally from the first catch member and arranged to engage the engagement member when the outer shield reaches the needle-containing position. As best shown in FIGS. 2, 5, and 13, the finger flange 38 is provided with interior surfaces 61 and 63 that serve as the second catch members for the shield 94, as will be explained below. While in the preferred embodiment the second catch member is associated with the finger flange 38, it should be obvious to one skilled the art that it can be located anywhere that will prevent continued shield movement, for example, anywhere along slot 46, 50.

Shield 94 does not have an operatively positioned member, for example, it does not have an outwardly extending finger gripping flange, preferably not within its rearward one-half, and most preferably not within its rearward one-third. Operatively positioned is defined as in a location that would allow a user to keep the shield effectively retracted with their fingers once released. Cap collar 19 is not considered to be an outwardly extending finger gripping flange as it is located beyond effective finger reach during use. For comparison, see the barrel finger flange 38.

The plunger assembly 17 comprising plunger rod 18 extends within the open rear end of the syringe barrel 14 and is reciprocally disposed therein. The plunger is releasably connected at its rounded and reduced diameter first end to a dislodgeable stopper 62 positioned within the reservoir of the syringe barrel 14. The stopper 62 is sometimes referred to as the "rubber piston" or "rubber stopper" and may be molded of a suitable biocompatible material. The stopper 62 may be collapsible or compressible. The shank of the plunger 18 extends out of the open rear end of the syringe barrel 14 includes a thumb pad 66 or thumb press area for receiving delivery pressure for pressing the plunger into the syringe barrel to deliver the fluid, e.g., medicament. The terms "thumb pad" and "thumb press area" are used interchangeably herein and designate a region coupled to or otherwise formed on an end of the plunger and which may be depressed by the thumb 70 (FIG. 1) or finger of a user during use of the medical device. The plunger 18 may be formed of a suitable molded plastic.

FIGS. 1-5 depict the safety syringe assembly 10 generally in a condition in which it is assembled, packaged and shipped, e.g., prior to use. It can be seen that the hypodermic needle 22 is in an exposed state with the needle protected by the cap 30, and the plunger 18 is in an advanced position within the syringe barrel 14. The outer shield 94 is disposed in the retracted position over the syringe barrel 14 and is provided with a front opening 96 to allow the needle 22 to extend therethrough. Thus, in the illustrated example of FIGS. 1-5, the syringe 10 is ready to draw a fluid, e.g., a medicament, into the barrel 14, via the needle 22, for example, by retracting the plunger 18, e.g., in the direction of arrow 82 to the position illustrated in FIG. 9.

The syringe assembly may be pre-filled with a fluid, e.g., a medicament. Alternatively, as shown in FIG. 9, the fluid may be withdrawn from a storage vial 74 having a membrane 78 sealed to the upper end thereof. That is, the vial 74 containing the fluid is inverted and the tip 26 of the needle 22 is pierced through the membrane 78. The fluid, e.g., the medicament, is withdrawn from the vial into the syringe barrel 14 by moving the plunger 18 in the direction of arrow 82 in FIG. 9. Thereafter, once a designated amount of fluid is withdrawn into the syringe barrel 14, the needle may be removed from the vial and the syringe device is ready for use on a patient. Referring now to FIG. 10, the contents of syringe barrel 14 may be injected into an injection site 86, such as any subcutaneous or intra-muscular location on a person where an injection is needed. Injection surface 91 is the skin above injection site 86. The user causes needle 22 to pierce the skin 91 above the injection site 86. The user places his fingers 42 on the outwardly extending finger flanges 38 using his thumb 70 on the thumb pad 66 applies pressure to press the plunger 18 into the syringe barrel 14 along the injection stroke to expel the fluid, e.g., medicament through the needle 22 and deliver the fluid into the injection site 86 of the person. As best shown in FIG. 5, the plunger 18 will travel through the injection stroke within the syringe barrel 14 until it reaches a terminus within the syringe barrel 14 at which point the medicament has been expelled through the needle 22 into the injection site 86.

A driving member, such as an elastic or resilient biasing means, here illustrated as a compression spring 90 of very small diameter and preferably made from stainless steel or other metal, is mounted over a reduced diameter nozzle 34. Referring now to FIGS. 1-4, the compression spring 90 is of such a diameter that it also fits within the interior of an outer shield 94 that is disposed over the syringe barrel 14. The compression spring 90 is provided for urging the outer shield 94 from a retracted position wherein the compression spring 90 is in a compressed state and the hypodermic needle 26 is exposed (FIGS. 1-5) to a needle-containing position wherein the outer shield 94 extends forwardly to cover the needle 22, which is best shown in FIG. 13. To retain the outer shield 46 in the retracted position, the outer shield 46 includes an engagement member, for example, a pair of opposed hook members 98 and 102 (best seen in FIGS. 2, 3, and 9) that extend rearwardly. The hook members 98 and 102 are arranged to engage the catch members 54 and 58 of the syringe barrel 14 to retain the outer shield 94 over the syringe barrel 14 in the retracted position. In particular, referring now to FIG. 5, hook member 98 is provided with a rear facing ramp 98a and a front facing ramp 98b defining a slot therebetween in which the catch 54 is arranged to be held captive when the shield 94 is retracted. Hook member 102 is provided with a rear facing ramp 102a which is arranged to engage catch 58 for the same purpose.

Referring now to FIGS. 2 and 5, plunger rod assembly 17 comprises plunger rod 18, thumb pad 66, and plunger rod assembly release member 106. In a preferred embodiment, extending forwardly from the thumb pad 66 is the plunger rod assembly release member, for example, release collar 106 including an inclined surface 110 (best shown in FIG. 5). Release member 106 may also be, for example, tabs comprising an inclined surface. (not shown).

As best demonstrated for comparison purposes in FIGS. 5 and 12, as the thumb pad 66 is pressed in the direction of the injection stroke and the plunger is moved towards and reaches its terminus within the syringe barrel, the inclined surface 110 of the release collar 106 (release collar inclined surface) will contact and apply force to the inclined surfaces 98a and 102a of the hook members deflecting them inwardly and causing them to release from the catches 54 and 58 of the syringe barrel 14 as the plunger 18 is pushed further along in the direction of the injection stroke. Once the inward moving releasing member, for example, hook members 98 and 102 clear the catches 54 and 58, the compressed spring 90 will expand to its normal position thus causing the outer shield 94 to move from its retracted position (FIGS. 11 and 12) to a needle-containing position (FIG. 13). Optionally, the syringe assembly 10 may be arranged such that a suitable amount of pressure must be applied in the direction of the injection stroke to cause the stopper 62 to compress slightly or distort against the interior wall of the syringe barrel 14 before the hook members 98 and 102 will release from the catches 54 and 58. FIG. 5 illustrates the stopper 62 in an undistorted condition while FIGS. 11 and 12 illustrate the stopper 62 in a compressed or distorted condition (distortable stopper). In this manner, the outer shield 94 will not move from its retracted position to cover the needle 22 until after all fluid, e.g., medicament, has been dispensed from the syringe barrel 14.

Referring now to FIG. 13, as the outer shield 94 travels to the needle-containing position, the hook member 98 will again deflect inwardly as the ramp 98b travels around catch surface 61 of finger flange 38. The hook member 98 will return to its undeflected positions to retain the catch member 61 between ramps 98a and 98b. Ramp 98a and hook 102 serve to stop forward movement of the outer shield 46 beyond the needle-containing position while ramp 98b prevents backward movement of the outer shield 94 towards the retracted position, thus locking the outer shield in the needle-containing position. In the needle-containing position the entire needle 22 including the tip 26 is safely housed within the shield 94. As best shown in FIGS. 2 and 8, the surface of the outer shield 94 is provided with a magnifier 107 on opposed sides thereof. The magnifier 107 extends over the length of the volume measuring indicia 44 located on the surface of the syringe barrel 14 and magnifies said indicia 44 to ease reading of said indicia 44.

Referring now in detail to the various figures of the drawings wherein like reference characters refer to like parts, there is shown at 200 in FIGS. 14 through 17 a second embodiment safety syringe assembly that includes a syringe barrel 214, a plunger 218, and a hypodermic needle 222 having a needle tip 226. The syringe 200 also includes a removable needle protector cap 230 (FIGS. 14, 15) arranged to snap onto the distal end of the safety syringe assembly 200.

The syringe barrel 214 defines a reservoir within which a fluid, e.g., a medicament, may be contained and dispensed therefrom. The barrel 214 has an outwardly extending flange 238 located towards the proximal end of the barrel 214 which facilitates gripping of the barrel with the user's fingers 242 (FIG. 14) when it is desired to move the plunger 218 relative to the barrel 214 linearly for normal use, such as when moving the plunger 218 through an injection stroke to inject a fluid, e.g., a medicament into a patient. The finger flange 238 may be annular or oblong. The portion of the syringe barrel 214 forward of the finger flange 238 is substantially transparent and includes volume measuring indicia 240 (FIG. 14) on the surface thereof to enable a user to determine the volume of fluid within the barrel 214. Referring now to FIGS. 15 and 17, at its most distal end, the barrel 214 includes an open nozzle 216 in which a needle-carrier 274 is positioned. Referring now to FIGS. 14-17, as the syringe barrel 214 extends rearwardly from the finger flange 238, it is slightly larger in diameter than the barrel extending forward from the finger flange 238.

The plunger 218 extends within the open rear end of the syringe barrel 214 and includes a first end with a stopper 262 positioned within the reservoir of the syringe barrel 214. The stopper is adapted to provide a slideable seal with the interior surface of the syringe barrel for expelling fluids through the distal end of the syringe barrel 214. The stopper 262 is in fluid tight engagement with the interior surface. The stopper 262 is preferably made of pliable rubber, thermoplastic rubber, plastic, or similar material. The stopper 262 is sometimes referred to as the "rubber piston" or "rubber stopper". Preferably, the stopper 262 may be substantially non-compressible. A second end of the plunger 218 extending out of the open rear end of the syringe barrel 214 includes a thumb pad 266 or thumb press area for receiving delivery pressure for pressing the plunger into the syringe barrel to deliver the fluid, e.g., medicament. The stopper 262 may be depressed by the thumb 270 (FIG. 14) or finger of a user during use of the syringe device. As shown in the figures, the diameter of the stopper 262 is approximately equal to the inside diameter of the syringe barrel 214 it extends into.

Referring now to FIGS. 15 through 17 and 22-25, the hypodermic needle 222 is held within the needle-carrier 274. The needle-carrier 274 comprises a generally tubular body having a through hole provided at its center for securing the hypodermic needle 222 therein. The needle-carrier 274 includes a smaller diameter fore section 278 in which a slot 282 is located, a comparatively larger diameter midsection 286, on which a pair of opposed grooves 290 are provided, and a "t-head" aft section 294 including an annular groove over which a generally cylindrical seal 298 may be positioned and retained. The seal 298, formed of a suitable biocompatible material, is adapted to provide a watertight fit with the interior surface of the syringe barrel 214 so that fluid in the barrel reservoir is directed into the needle 222 for delivery to the injection site of the person. As mentioned above, the needle-carrier 274 is positioned within the open nozzle 216 of the syringe barrel 214 and is retained therein by a pivotable locking projection 302 disposed at the distal end of the syringe barrel 214. The locking projection 302 is arranged to extend radially inwardly and lodge within the slot 282 of the needle-carrier 274 to retain the needle-carrier 274 in a retained position and to prevent movement of the needle-carrier 274 in the proximal direction with respect to the syringe body 214. The needle-carrier is shown in this retained position with the locking projection 302 lodged within the slot 282 in FIGS. 16, 17, 20, and 21.

Figure 14:
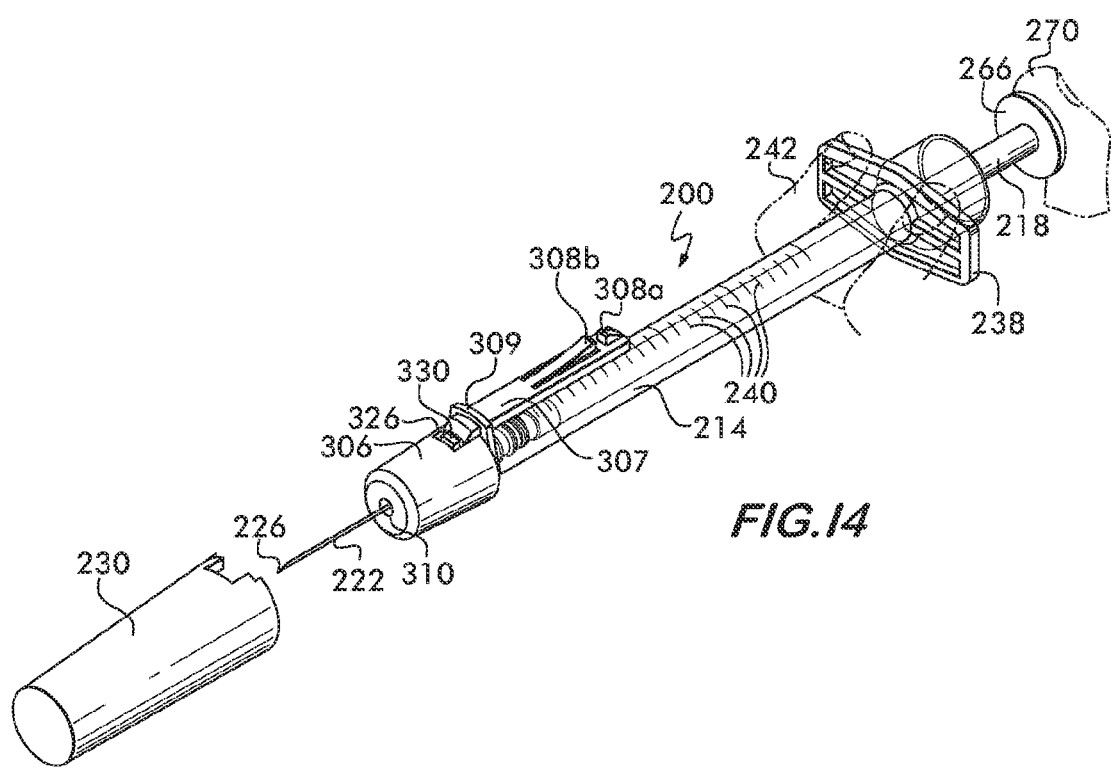
FIG. 14 is a perspective view of a second embodiment of the present invention.

Referring now to FIGS. 14, 16 and 17, an outer shield 306 is shown disposed in a retracted position over the syringe barrel 214 and is provided with a front opening 310 to allow the needle 222 to extend therethrough. The outer shield 306 also includes a rearward extending arm 307 that extends over the outer surface of the syringe body 214 and includes an inclined stop 308a and a latching projection 308b that are spaced a predetermined distance from each other to define a space therebetween. The latching projection 308b is formed of a resilient material and is downwardly deflectable. The rearward extending arm 307 extends through an upstanding collar 309 integral with and extending radially outwardly from the syringe body 214. Alternatively, the upstanding collar 309 could be designed to be rotatable around the syringe body 214 to allow the rearward extending arm 307 to be adjusted to any location that is desirable.

Referring now to FIG. 20, the syringe device 200 is ready to draw a fluid, e.g., a medicament, into the barrel 214, via the needle 222, for example, by retracting the plunger 218, e.g., in the direction of arrow 301 to the position illustrated in FIG. 20 in the manner as described above to withdraw a medicament from a vial. Referring now to FIG. 21, the contents of syringe barrel 214 may be injected into an injection site 314, in the manner previously described above by the user placing his fingers 242 on the outwardly extending finger flange 238 and using his thumb 270 on the thumb pad 266 to apply pressure to the plunger 218 to deliver medicament to the injection site 314. As best shown in FIGS. 20 and 21, the plunger 218 will travel through the injection stroke 318 within the syringe barrel 214 until it contacts the needle-carrier 274 and all the medicament has been expelled through the needle 222 into the injection site 314.

A driving member, such as an elastic or resilient biasing means, here illustrated as a compression spring 322 of very small diameter and preferably made from stainless steel or other metal, is mounted over the open nozzle 216 of the syringe barrel 214. Referring now to FIGS. 16 and 17, the compression spring 322 is shown in a compressed state therein and is of such a diameter that it also fits within the interior of an outer shield 306 that is disposed over the syringe barrel 214. The compression spring 322 is provided for urging the outer shield 306 from a retracted position wherein the compression spring 322 is in a compressed state and the hypodermic needle 226 is exposed (e.g., FIGS. 20 and 21) to a needle-containing position wherein the outer shield 306 extends forwardly to cover the needle 322, which is best shown in FIGS. 24 and 25.

Referring now to FIG. 17, to retain the outer shield 306 in the retracted position, the outer shield 306 includes opposed slots 326 through which opposed deformable members 330 located on the barrel 214 extend. The upright deformable members 330 are integral with the syringe barrel 214 and extend radially outwardly therefrom and through slots 326 to retain the outer shield 306 in the retracted position. The deformable members 330 remain in an upright orientation so long as they are supported by the body of the needle-carrier 274 located thereunder. As best shown in FIG. 17, the deformable members 330 remain in an upright position because they are supported by the larger diameter midsection 286 of the needle-carrier. Referring now to FIGS. 17 and 22 for comparison purposes, as the thumb pad 266 is pressed in the direction of the injection stroke 318 and the plunger 218 is moved distally, it eventually contacts the t-head aft section 294 of the needle-carrier 274. Referring now to FIG. 22, further movement of the plunger 218 in the direction of the injection stroke 318 causes the needle-carrier 274 to move distally within the open nozzle 216 from its retained position to a forward position. As best shown in FIGS. 22 and 23, distal movement of the needle-carrier 274 causes the pivotable locking projection 302 to pivot out of the slot 282 of the needle-carrier 274.

Referring now to FIG. 22-25, as the needle-carrier 274 moves from its retained position to its forward position, the opposed grooves 290 of the needle-carrier 274 move under the deformable members 330, thus removing support for the deformable members 330 which can no longer remain upright. As a result, the deformable members 330 can no longer engage the outer shield 306 and retain the outer shield in the retracted position. As the compression spring 322 pushes the outer shield 306 to the needle-containing position, the deformable members 330 collapse within the opposed grooves 290 of the needle-carrier 274. FIG. 23 illustrates the compression spring 322 beginning to move the outer shield 306 to its needle-containing position as the deformable members 330 have collapsed within the opposed grooves 290. FIGS. 24 and 25 illustrate the outer shield moved to the needle-containing position to shield the needle tip 226. As the outer shield 306 moves to the needle-containing position, the length of the rearward extending arm 307 moves distally through the upstanding collar 309. As the latching projection 308b passes through the collar 309, it deflects downwardly to pass through the collar 309. Once the latching projection 308b has passed through the collar 309, it returns to its undeflected position to hold captive the collar 309 in the space located between the inclined stop 308a and the latching projection 308b, thus locking the outer shield 306 in the needle-containing position over the needle 222.

Referring now in detail to the various figures of the drawings wherein like reference characters refer to like parts, there is shown at 400 in FIGS. 26 through 36 a third embodiment safety syringe assembly that includes a syringe barrel 414, a plunger 418, and a hypodermic needle 422 having a needle tip 426. The syringe 400 also includes a removeable protector cap 430 arranged to snap onto the distal end of the safety syringe assembly 400.

The syringe barrel 414 defines a reservoir within which a fluid, e.g., a medicament, may be contained and dispensed therefrom. The barrel 414 has an outwardly extending flange 438 located towards the proximal end of the barrel 414 which facilitates gripping of the barrel with the user's fingers 442 (FIG. 26) when it is desired to move the plunger 418 relative to the barrel 414 linearly for normal use, such as when moving the plunger 418 through an injection stroke indicated at arrow 417 (FIG. 33) to inject a fluid, e.g., a medicament into a patient. The finger flange 438 may be annular or oblong (as shown). The portion of the syringe barrel 414 forward of the finger flange 438 is substantially transparent and includes volume measuring indicia 440 (FIGS. 26 and 27) on the surface thereof to enable a user to determine the volume of fluid within the barrel 414. Referring now to FIGS. 27 and 29, disposed within the distal opening 416 of the syringe barrel 414 is a reduced diameter internal nozzle 415, the internal nozzle being tapered distally and integral with the syringe barrel 414. As best shown in FIG. 29, the internal nozzle 415 includes a central opening 428 that extends axially and is in fluid communication with the reservoir of the syringe barrel 414.

Referring again to FIGS. 27 and 29, a needle-carrier 474 is disposed over the internal nozzle 415 at the distal end of the syringe barrel 414 and may be secured to the distal end by any suitable means, e.g., threads disposed on the internal surface of the distal opening 416. The needle-carrier 474 comprises a generally tapered tubular body including ribs 475 (FIG. 27) and includes an axially extending through-hole provided at its center for securing the hypodermic needle 422 therethrough. As best shown in FIGS. 27, 29 and 35, the needle-carrier 474 includes a support surface 478 for supporting a driving member, such as an elastic or resilient biasing means, here illustrated as a compression spring 490 of very small diameter and preferably made from stainless steel or other metal. For example, the compression spring 490 may be of frusto-conical shape having a wider end supported by the support surface 478 and a narrower end supported by an inner-step or support surface 431a provided on the interior surface of the outer shield 431 (FIG. 35). The needle-carrier 474 also includes a pair of radially extending projections 476 arranged for retaining the outer shield 431 thereover in the manner discussed below.

Referring again to FIGS. 27 and 29, the outer shield 431 is arranged to be disposed over the needle-carrier 474 and compression spring 490 and retained thereover in an engaged position. To this end, the outer shield 431 is provided with a pair of opposed and outwardly flaring wings 433, each wing including a through-slot 435 at a base portion thereof. The through-slot 435 is sized and located to allow passage of the opposed radially extending projections 476 of the needle-carrier 474 therethrough to retain the outer shield 431 in an engaged position over the needle-carrier 474 and compression spring 490. When the outer shield 431 is in the engaged position, the compression spring is in a compressed state and the hypodermic needle 422 extends through a central opening 496 in the outer shield 431 thus exposing the needle 422 for drawing fluids into the syringe barrel and expelling fluids through the needle 422 at an injection site. Upon release of the outer shield 431 from the engaged position (described in detail below), the compressed spring 490 extends to its normal position and drives the outer shield 431 to a needle-containing position, as best shown in FIGS. 35-36.

A release ring 419 is provided to fit snugly over the distal end of the syringe 414 and includes a plurality of radially inward extending tabs 421. The inwardly extending tabs 421 are arranged to extend into elongated slots 423 also located at the distal end of the syringe barrel 414. The slots 423 are somewhat elongated in length so that when the tabs 421 are disposed therein, the release ring 419 is slideable in an axial direction a short predetermined distance over the syringe barrel 414 between a retained position and a releasing position. As best shown in FIG. 29, when in the retained position, the inwardly extending tabs 421 of the release ring 419 are positioned at the proximal end of the slots 423. As best shown in FIGS. 34-36, when in releasing position, the inwardly extending tabs 421 of the release ring 419 are positioned at the distal end of the slots 423. The release ring 419 is provided with an annular release projection 425 that includes a forward facing annular ramp 427 (best seen in FIGS. 35 and 36). When the release ring 419 is in the retained position, the annular ramp 427 is arranged to abut the outwardly flaring wings 433 of the outer shield 431. When the release ring 419 is slid axially to the releasing position, the annular ramp 427 engages the wings 433 outwardly releasing them from the extending projections 476 thus causing the outer shield 431 to spring to a needle-enclosing position.

The plunger 418 extends within the open rear end of the syringe barrel 414 and includes a first end with a stopper 462 positioned within the reservoir of the syringe barrel 414. The stopper 462 is adapted to provide a slidable seal with the interior surface of the syringe barrel 414 for expelling fluids through the distal end of the syringe barrel 414. The stopper 462 is in fluid tight engagement with the interior surface of the syringe barrel 414. The stopper 462 is preferably made of suitable materials as described in connection with the earlier embodiments, and may be substantially non-compressible. A second end of the plunger 418 extending out of the open rear end of the syringe barrel 414 includes a thumb pad 466 or thumb press area for receiving delivery pressure for pressing the plunger into the syringe barrel 414 to deliver the fluid, e.g., medicament. The thumb press 466 may be depressed by the thumb 470 (FIG. 26) or finger 442 of a user during use of the syringe device. As shown in the figures, the diameter of the stopper 462 is approximately equal to the inside diameter of the syringe barrel 414 extending rearwardly therefrom.

Referring now to FIG. 32, the syringe device 400 is ready to draw a fluid, e.g., a medicament, into the barrel 414, via the needle 422 from a vial 403, for example, by retracting the plunger 418, e.g., in the direction of arrow 401 to the position illustrated in FIG. 32 in the manner as described in earlier embodiments to withdraw a medicament from the vial 403. Referring now to FIG. 33, once the fluid is drawn into the syringe barrel 414, the contents of the syringe barrel 414 may be injected into an injection site such as any subcutaneous or intra-muscular location on a person where an injection is needed.

The contents of syringe barrel 414 is injected in the manner previously described by the user placing his fingers 442 on the outwardly extending finger flange 438 and using his thumb 470 on the thumb pad 466 to apply pressure to the plunger 418 to deliver medicament to the injection site. As best shown in FIGS. 29, 33 and 34, as the plunger 418 travels through the injection stroke (arrow 417), within the syringe barrel 414 the plunger stopper 462 eventually abuts and exerts pressure in the distal direction upon a seal 508 located within the syringe barrel 414. The seal 508 may include an annular groove, is generally cylindrical, and provides a watertight fit with the interior surface of the syringe barrel 414. In turn, the seal 508 exerts force against the inwardly extending tabs 421 of the release ring 419 to push the release ring 419 within the slot 423 of the syringe barrel 414 from the proximal side to the distal side of the slot 423.

As the release ring 419 moves distally, its forward facing annular ramp 427 applies force to the outwardly flared wings 433 of the outer shield 431 driving the wings 433 radially outward and eventually lifting the wings 433 above the radially extending projections 476 of the needle-carrier 474. Referring now to FIGS. 35 and 36, once the wings 433 have cleared the tops of the projections 476, the outer shield 431 is no longer engaged by the projections 476 of the needle-carrier 474. As a result, as best shown in FIGS. 35 and 36, the compressed spring 490 expands to its normal position and drives the outer shield 431 to a needle-containing position. As the outer shield 431 moves to the needle-containing position, the central opening 496 will travel distally over the needle 422 and beyond the needle tip 426 to safely contain the needle within the outer shield 431.

Referring now to FIGS. 27, 35 and 36, a limit ring 500 is shown. In FIGS. 35 and 36, the limit ring 500 is shown mounted in abutting relation with a stepped portion of the outer shield 431. As can best be seen in FIG. 27, the limit ring 500 is provided with a proximally extending finger 512 that is arranged to extend within a slot 516 in the outer shield 431 to assure the snug mounting of the limit ring 500 over the shield 431. The limit ring 500 also includes a laterally extending tab 502 that is connected to a tether 520 which connects the limit ring 500 to the needle-carrier 474 (best seen in FIG. 36), the tether 520 being of a pre-selected length. The tether 520 may be of a construction that includes multiple hinges enabling it to fold and unfold therealong. Alternatively, a tether 524 may be formed of a bendable material. As the outer shield 431 moves from the engaged position to the needle-containing position, the tethered limit ring 500 will limit movement of the outer shield 431. In other words, the limit ring 500 will prevent the outer shield 431 from moving beyond the needle tip 426 and assure that the entire needle 422 including the tip will be contained within the outer shield 431 so as to prevent exposure to a contaminated needle. As best shown in FIG. 36, when moved to the needle-containing position, the outer shield 431 is in an off-set position with respect to the needle tip 426. This is due to the fact that the spring 490 is mounted over the needle-carrier 474 in a slightly offset position due to the inclusion of the support surface 478 (FIG. 35) which does not extend radially around the entire needle-carrier 474. In this manner, the needle tip 426 is offset from the central opening 496 of the outer shield 431 to prevent inadvertent contact with the contaminated needle.

Referring now in detail to the various figures of the drawings wherein like reference characters refer to like parts, there is shown at 600 in FIGS. 37 through 47A a fourth embodiment safety syringe assembly that includes a syringe barrel 614, a plunger 618, and a hypodermic needle 622 having a needle tip 626. The syringe assembly 600 includes a needle protector cap 624 (FIG. 38) arranged to snap onto the distal end of the safety syringe assembly 600 to protect the needle prior to use. The deployable outer shield 630 is arranged to move in response to thumb actuation from a retracted position (best shown in FIGS. 37, 39, 40, 43, and 44) to a needle-protecting position (best shown in FIG. 47). As best shown in FIGS. 37 and 39, the surfaces of the outer shield 630 include a raised or thickened portion arranged to be disposed over the indicia 643 of the syringe 614. This raised or thickened portion extends over the length of the volume measuring indicia 643 and provides magnification to ease reading of said indicia 643.

Figure 40:
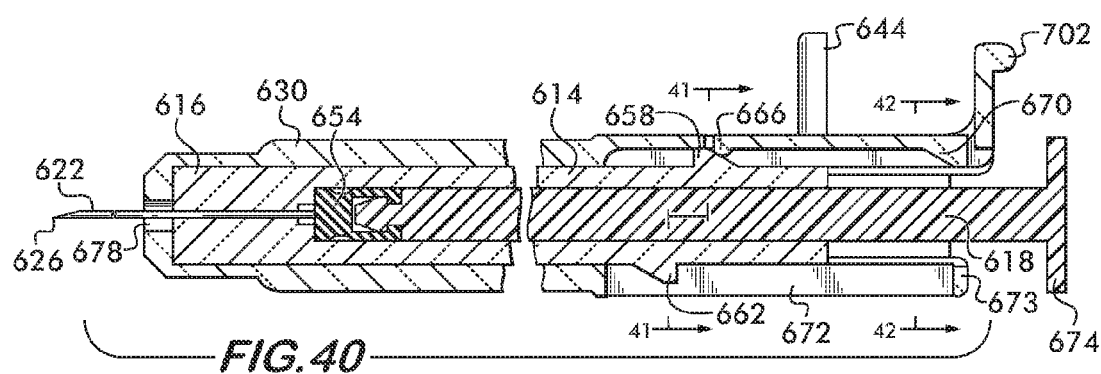
FIG. 40 is an enlarged cross-sectional view of the fourth embodiment of the present invention showing the outer shield disposed in the retracted position.
Figure 41:
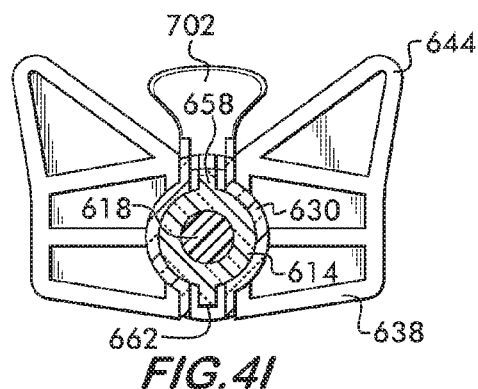
FIG. 41 is a cross-sectional view taken along line 41-41 of FIG. 40.
Figure 42:
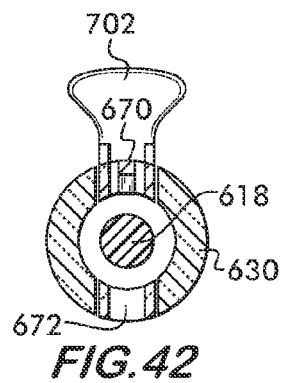
FIG. 42 is a cross-sectional view taken along line 42-42 of FIG. 40.

As best shown in FIG. 40, the syringe barrel 614 includes a forward end nozzle 616 having a reduced diameter axial opening in which the needle 622 is mounted, and a rear end including a reservoir 632 (FIG. 43) within which a fluid, e.g., a medicament, may be contained. The needle 622 or needle cannula (those terms being used interchangeably herein) includes a forward tip 626 and is in fluid communication with the reservoir 632 through the reduced diameter nozzle 616.

As best seen in FIG. 38, the syringe barrel 614 includes an outwardly extending flange 638 located towards the proximal end of the barrel 614 which facilitates gripping of the barrel 614 with the user's fingers 642 (FIG. 37) when it is desired to move the plunger 618 relative to the barrel 614 linearly for normal use, such as when moving the plunger 618 through an injection stroke to inject a fluid, e.g., a medicament into a patient. The finger flange 638 may be annular or oblong. The finger flange 638 is provided with upstanding ears 644. Together, the finger flange 638 and upstanding ears 644 are provided to enable the user to position and retain the barrel 614 within fingers 642 (FIG. 37) while using the thumb 677 to move the plunger 618 through the injection stroke. Upon completion of the injection stroke, if it is desired to deploy the outer shield 630 to the needle-protecting position, the user moves the thumb 677 from the thumb pad 674 of the plunger 618 and depresses an actuation member 702 located in close proximity to the thumb pad 674. Due to the close proximity between the thumb pad 674 and the actuation member 702, movement of the thumb 677 from the plunger thumb pad 674 to the actuation member 702 is an easy transition. Also, this proximity between the thumb pad 674 and the actuation member 702 eliminates the need for the user to reposition fingers 642 on the finger flange 638 or on any other part of the embodiment during this transition, thus enabling the user to maintain the syringe barrel 614 in a relatively safe position during this transition to avoid accidental needle tip pricks after withdrawal from patients.

The portion of the syringe barrel 614 forward of the finger flange 638 is substantially transparent and includes volume measuring indicia 643 (FIG. 38) on the surface thereof to enable a user to determine the volume of fluid within the barrel 614. For example, the syringe barrel 614 may hold up to 3.0 ml in volume, however, may hold other volumes greater or lesser. As best shown in FIG. 38, the syringe barrel 614 includes a cylindrical wall 646 that extends rearward from the finger flange 638 and is somewhat larger in diameter than the forward portion of the syringe barrel 614 and includes a slot 650 bounded by the cylindrical wall 646. As best shown in FIGS. 38 and 39, an upper catch 658 is located on the top side of the syringe barrel 614 and includes an inclined surface that faces towards the syringe barrel proximal end while a lower catch 662 located on the bottom side of the syringe barrel 614 includes an inclined surface that faces towards the syringe barrel distal end. The upper catch 658 is arranged for engaging a forward extending deflectable member 666 and a rearward extending deflectable member 670, both members being resiliently deflectable and located on the top surface of the deployable outer shield 630. The lower catch 662 is situated within an elongated slot 672 located on the bottom portion of the outer shield 630. The elongated slot 672 is bounded by a peripheral wall including an end wall 673 that serves as a stop to limit movement of the outer shield 630 beyond a needle-containing position.

The plunger 618 extends within the open rear end of the syringe barrel 614 and includes a first end with a stopper 654 positioned within the reservoir of the syringe barrel 614. The stopper 654 is preferably substantially non-compressible. A second end of the plunger 618 extending out of the open rear end of the syringe barrel 614 includes a thumb pad 674 or thumb press area for receiving delivery pressure for pressing the plunger into the syringe barrel to deliver the fluid, e.g., medicament. The terms "thumb pad" and "thumb press area" are used interchangeably herein and designate a region coupled to or otherwise formed on an end of the plunger and which may be depressed by the thumb 677 or finger of a user during use of the medical device.

Referring now to FIGS. 37, 39 and 40, the safety syringe assembly 600 is shown therein generally in a condition in which it is ready for use. That is, in these figures, it can be seen that the hypodermic needle 622 is in an exposed state where it can be protected by the cap 624, and the plunger 618 is in an advanced position within the syringe barrel 614. The outer shield 630 is disposed in the retracted position over the syringe barrel 614. Referring now to FIG. 43, the outer shield 630 is provided with a front opening 678 to allow the needle 622 to extend therethrough. The syringe 600 is ready to draw a fluid, e.g., a medicament, into the barrel 614, via the needle 622, for example, by retracting the plunger 618, e.g., in the direction of arrow 682 to the position illustrated in FIG. 43.

The syringe assembly may be pre-filled with a fluid, e.g., a medicament. Alternatively, as shown in FIG. 43, the fluid may be withdrawn from a storage vial 686 having a membrane 690 sealed to the upper end thereof. That is, the vial 686 containing the fluid is inverted and the tip 626 of the needle 622 is pierced through the membrane 690. The fluid, e.g., the medicament, is withdrawn from the vial into the syringe barrel 614 by moving the plunger 618 in the direction of arrow 682 in FIG. 43. Thereafter, once a designated amount of fluid is withdrawn into the syringe barrel 614, the needle may be removed from the vial and the syringe device is ready for use on a patient. Referring now to FIG. 44, the contents of syringe barrel 614 may be injected into an injection site 694, such as any subcutaneous or intra-muscular location on a person where an injection is needed. The user causes needle 622 to pierce the skin above the injection site 694. The user places his fingers 642 on the outwardly extending finger flanges 638 and using his thumb 677 on the thumb pad 674 applies pressure to press the plunger 618 into the syringe barrel 614 along an injection stroke indicated by arrow 698 to expel the fluid, e.g., medicament through the needle 622 and deliver the fluid into the injection site 694 of the person. As best shown in FIG. 44, the plunger 618 will travel through the injection stroke within the syringe barrel 614 until it reaches a terminus within the syringe barrel 614 at which point it can travel no further and all of the medicament has been expelled through the needle 622 into the injection site 694.

Figure 45:
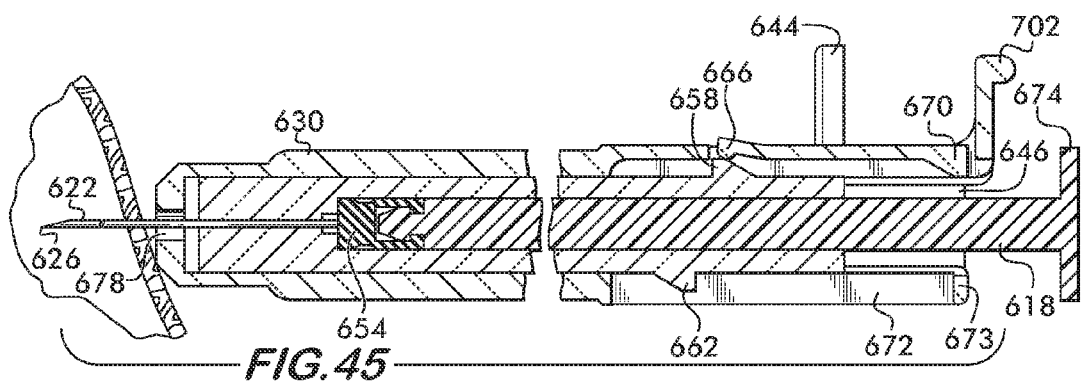
FIG. 45 is an enlarged cross-sectional view of the fourth embodiment of the present invention showing the outer shield being deployed towards the needle-containing position.
Figure 46:
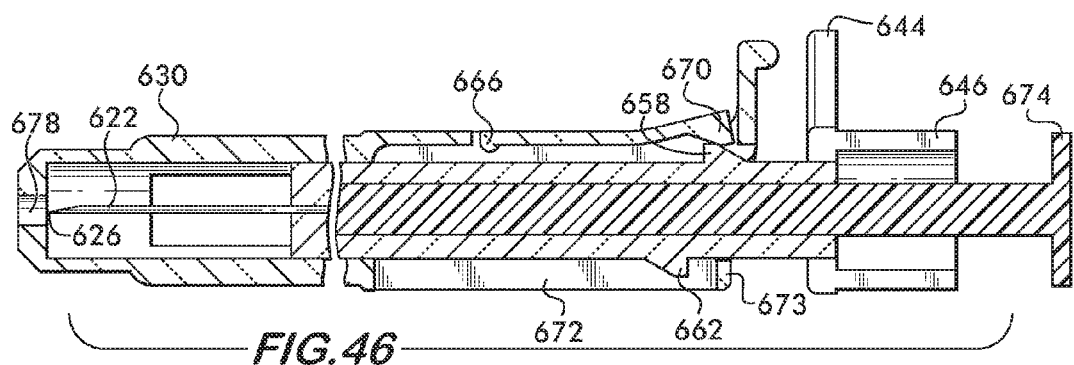
FIG. 46 is an enlarged cross-sectional view of the fourth embodiment of the present invention showing the outer shield moving towards the needle-containing position.
Figure 47:
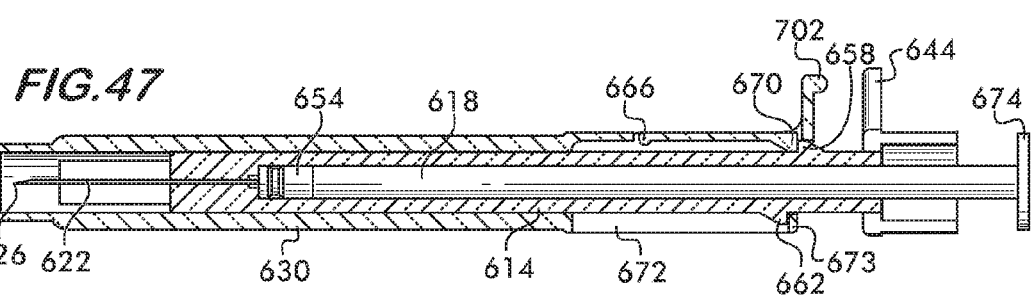
FIG. 47 is a cross-sectional view of the fourth embodiment of the present invention showing the outer shield deployed in the needle-containing position.

The outer shield 630 is provided with an upwardly extending actuation member 702 which is provided for urging the outer shield 630 from the retracted position wherein the hypodermic needle 626 is exposed (FIG. 45) to a needle-containing position wherein the outer shield 630 extends forwardly to cover the needle 622, which is best shown in FIGS. 46 and 47. Referring now to FIG. 40, the outer shield 630 is shown retained in the retracted position as a result of the rounded surface of the forward extending deflectable member 666 of the outer shield 630 abutting the upper catch 658 of the syringe barrel 614. Once the plunger 618 has reached the terminus of the injection stroke, the user may deploy the outer shield 630. As mentioned above, upon completion of the injection stroke, if it is desired to deploy the outer shield 630 to the needle-protecting position, the user may readily move the thumb 677 from the thumb pad 674 of the plunger 618 to the actuation member 702 located in close proximity thereto. During this transition, the user can maintain the barrel 614 in a relatively safe orientation by keeping fingers 642 placed on the finger flanges 638.

Referring now to FIGS. 45-47, as thumb pressure is applied to the actuation member 702, the deflectable member 666 deflects outwardly as the rounded forward surface rides up and eventually clears the top surface of the upper catch 658. After the rounded forward surface of the deflectable member 666 has passed the upper catch 658, the deflectable member 666 returns to its undeflected position, thus permitting the outer shield 630 to be moved by thumb pressure to the needle-containing position. As the outer shield 630 is moved towards the needle-containing position, the inclined surface of the rear extending deflectable member 670 rides up and eventually clears the top surface of the upper catch 658. Once the deflectable member 670 has cleared the upper catch 658, it returns to its undeflected position and the lower catch 662 abuts the end wall 673 to lock the outer shield 630 in place in the needle-containing position to prevent inadvertent contact with the contaminated needle.

Figure 47A:
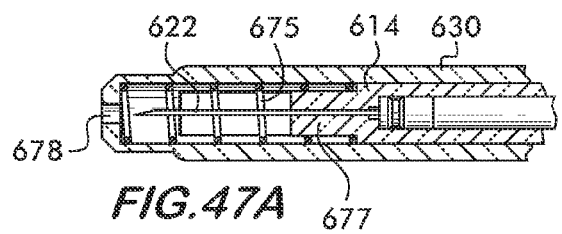
FIG. 47A is an enlarged cross-sectional view of a portion of a spring-loaded alternative version of the fourth embodiment of the present invention showing the outer shield deployed in the needle-containing position.

As best shown in FIGS. 38A, 39A, and 47A, alternatively, a compression spring 675 may be positioned in a compressed state between the front end of the syringe barrel 614 and the outer shield 630 when the outer shield is in the retracted position. As best shown in FIG. 38A, the compression spring 675 is sized in diameter to fit over a reduced diameter nozzle 677 located at the distal end of the syringe barrel 614. As thumb pressure is applied to the upwardly extending actuation member 702, the forward extending deflectable member 666 rides up and eventually clears the top surface of the upper catch 658. As the deflectable member 666 clears the top surface of the upper catch 658, the compressed spring 675 moves to its normal position, and propels the outer shield 630 from its retracted position to its deployed to lock the outer shield 630 in the needle-containing position as described above.

Referring now in detail to the various figures of the drawings wherein like reference characters refer to like parts, there is shown at 800 in FIGS. 48 through 53 a fifth embodiment safety syringe assembly that includes a syringe barrel 814, a plunger 818, and a hypodermic needle 822 having a needle tip 826. The syringe 800 also includes a removeable needle protector cap 830 (FIGS. 48, 49) arranged to snap onto the distal end of the safety syringe assembly 800 to protect against needle pricks when the outer shield 806 is in a retracted position.

Figure 48:
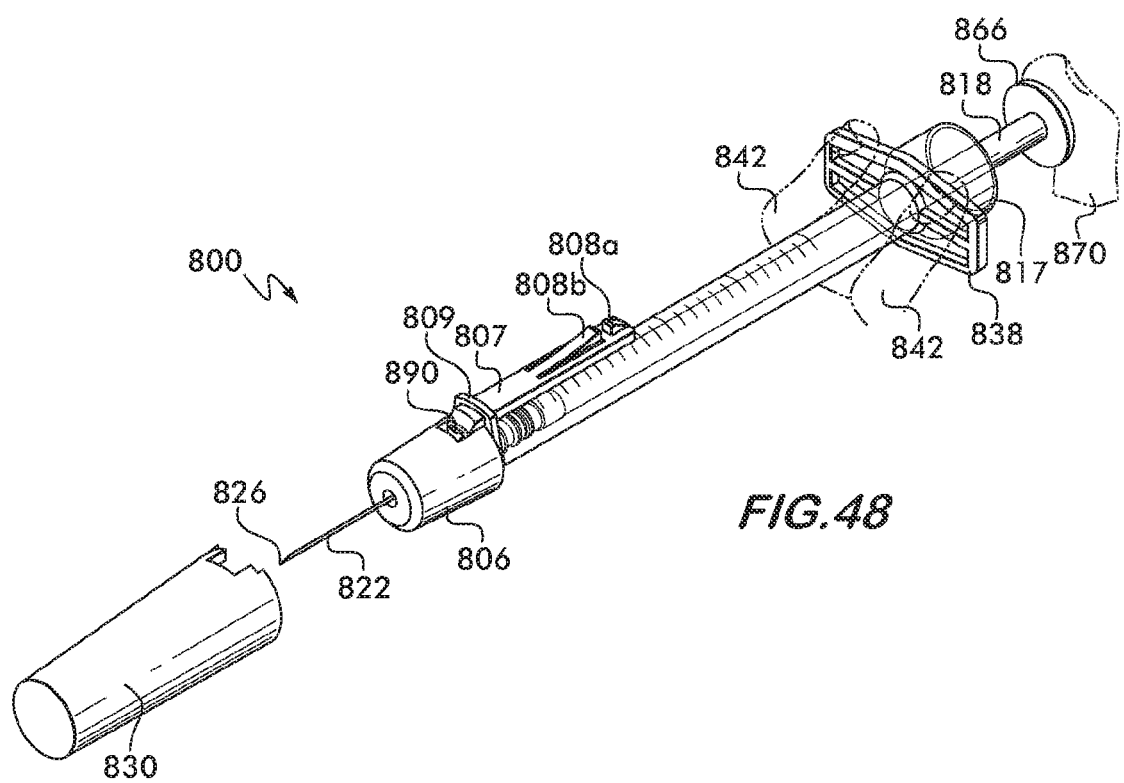
FIG. 48 is a perspective view of a fifth embodiment of the present invention.
Figure 49:
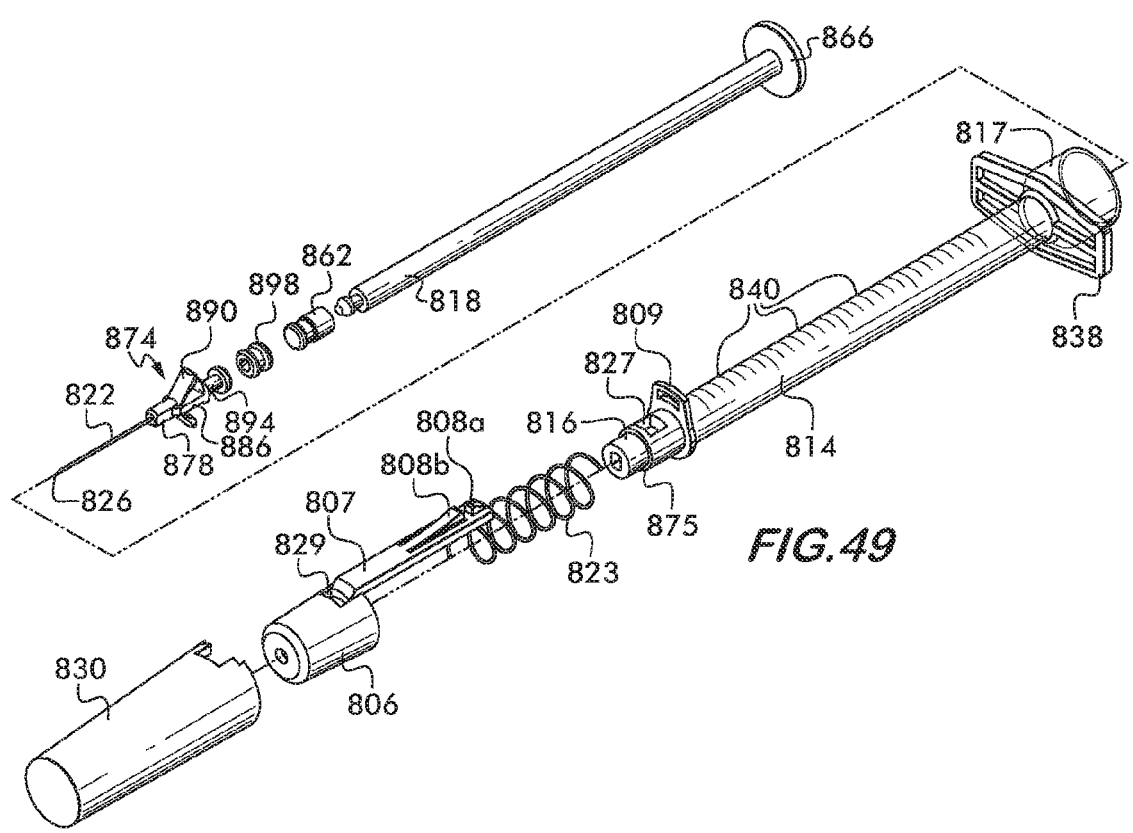
FIG. 49 is an exploded perspective view of the fifth embodiment of the present invention illustrating the components of this embodiment.

The syringe barrel 814 defines a reservoir within which a fluid, e.g., a medicament, may be contained and dispensed therefrom. The barrel 814 has an outwardly extending flange 838 located towards the proximal end of the barrel 814 which facilitates gripping of the barrel with the user's fingers 842 (FIG. 48) when it is desired to move the plunger 818 relative to the barrel 814 linearly for normal use, such as when moving the plunger 818 through an injection stroke to inject a fluid, e.g., a medicament into a patient. The finger flange 838 may be annular or oblong. The portion of the syringe barrel 814 forward of the finger flange 838 is substantially transparent and includes volume measuring indicia 840 (FIG. 49) on the surface thereof to enable a user to determine the volume of fluid within the barrel 814. Referring now to FIGS. 49, 50 and 51, a needle-carrier 874 is positioned within the barrel 814 at the distal end thereof.

The needle-carrier 874 is positioned within the barrel 814 at its open distal end 816. As best seen in FIGS. 48-49, as the syringe barrel 814 extends in the proximal direction from the finger flange 838, it is slightly larger in diameter at 817 than the barrel 814 extending forward from the finger flange 838.

The plunger 818 extends within the open rear end of the syringe barrel 814 and includes a first end with a stopper 862 positioned within the reservoir of the syringe barrel 814. The stopper 862 is adapted to provide a slidable seal with the interior surface of the syringe barrel for expelling fluids through the distal end of the syringe barrel 814. The stopper 862 is in fluid tight engagement with the interior surface. Preferably, the stopper 862 is substantially non-compressible. The proximal end of the plunger 818 includes a thumb pad 866 for receiving delivery pressure for pressing the plunger into the syringe barrel to deliver the fluid, e.g., medicament. The thumb pad 866 may be depressed by the thumb 870 (FIG. 48) or finger of a user during use of the syringe device.

Referring now to FIGS. 49 through 51, the hypodermic needle 822 is held within the needle-carrier 874. The needle-carrier 874 comprises a body having a through hole 815 provided at its center for securing the hypodermic needle 822 therein. The needle-carrier 874 includes a fore section 878 having generally square outer surface (FIG. 49), a mid-section 886 on which a pair of opposed wings 890 are provided, and an aft section 894 in the form of a "t-head". The t-head includes an annular groove over which a generally cylindrical seal 898 may be positioned and retained. The seal 898, formed of a suitable biocompatible material, is adapted to provide a watertight fit with the interior surface of the syringe barrel 814 so that fluid in the barrel reservoir is directed into the needle 822 for delivery to the injection site of the person.

As best shown in FIG. 50, the wings 890 are biased towards a deployed position. In this position, the wings retain the outer shield 806 in a retracted position over the distal end of the syringe barrel 814, thus exposing the needle 822. Referring now to FIGS. 50 through 52, the wings 890 are arranged to move from the deployed position (FIG. 50) to a collapsed position (FIG. 52) thus enabling the outer shield 806 to move from its retracted position to an extended position in a manner to be discussed in more detail below.

A driving member, such as an elastic or resilient biasing means, here illustrated as a compression spring 823 of very small diameter and preferably made from stainless steel or other metal, is mounted over a shoulder 875 of the syringe barrel 814, as best shown in FIG. 50. In FIG. 50, the compression spring 823 is shown in a compressed state and is of such a diameter that it fits within the interior of the outer shield 806 and is disposed over the syringe barrel shoulder 875. The compression spring 823 is provided for urging the outer shield 806 from the retracted position wherein the compression spring 823 is in a compressed state and the hypodermic needle 822 is exposed to a needle-containing position wherein the outer shield 806 extends forwardly to cover the needle 822, which is best shown in FIG. 52.

Referring again to FIG. 50, the outer shield 806 is shown disposed in a retracted position over the syringe barrel 814. The outer shield 806 also includes a rearward extending arm 807 that extends over the outer surface of the syringe body 814 and includes an inclined stop 808*a* and a latching projection 808*b* that are spaced a predetermined distance from each other to define a space therebetween. The latching projection 808*b* is formed of a resilient material and is downwardly deflectable. The rearward extending arm 807 extends through an upstanding collar 809 integral with and extending radially outwardly from the syringe body 814.

Referring again to FIG. 50, the syringe device 800 is ready to draw a fluid, e.g., a medicament, into the barrel 814, via the needle 822, for example, by retracting the plunger 818, e.g., in the direction of arrow labeled "FILL" 801 to withdraw a medicament from a vial. The contents of syringe barrel 814 may be injected into an injection site (not shown) in the manner previously described by the user placing fingers 842 on the outwardly extending finger flange 838 and using the thumb 870 on the thumb pad 866 to apply pressure to the plunger 818 to deliver medicament in the direction of the arrow labeled "INSERT" 803 to the injection site (not shown). Referring to FIGS. 50 and 51, the plunger 818 will travel through the injection stroke 803 within the syringe barrel 814 until it contacts the aft section 894 of the needle-carrier 874 and all the medicament has been expelled through the needle 822 into the injection site.

As best shown in FIGS. 49 and 50, the syringe barrel 814 is provided with opposed slots 827 through which the wings 890 may extend. Likewise, the outer shield 806 is provided with opposed slots 829 that align with the syringe barrel slots 827 when the outer shield 806 is in the retracted position. In this manner, the wings 890 may extend through the slots 827 and 829 to retain the outer shield 806 in the retracted position over the syringe barrel 814 and retain the compression spring 823 in a compressed state. Referring now to FIG. 51 for comparison purposes, as the thumb pad 866 is pressed in the direction of the injection stroke 803 and the plunger 818 is moved distally, it eventually contacts the aft section 894 of the needle-carrier 874. Further movement of the plunger 818 in the direction of the injection stroke 803 causes the needle-carrier 874 to move slightly in a distal direction within the distal open end 816 of the barrel 814. Such distal movement of the needle-carrier 874 causes the wings 890 to move from their deployed position to their collapsed position.

Referring now to FIGS. 51 and 52, as the needle-carrier 874 moves distally within the syringe barrel 814, the wings 890 move from their deployed position to the collapsed position, and out of engagement with the outer shield 806. Once the outer shield 806 becomes disengaged from the wings 890, the compression spring 823 pushes the outer shield 806 to the needle-containing position (FIG. 52). FIG. 51 illustrates the compression spring 822 beginning to move the outer shield 806 to its needle-containing position as the wings move to their collapsed position. As the outer shield 806 moves to the needle-containing position, the length of the rearward extending arm 807 moves distally through the upstanding collar 809. As the latching projection 808*b* passes through the collar 809, it deflects downwardly to pass through the collar 809. Once the latching projection 808*b* has passed through the collar 809, it returns to its undeflected position to prevent movement of the outer shield in the proximal direction away from the needle-containing position. Further movement of the outer shield 806 in the distal direction past the needle containing position is prevented due to the inclined stop 808*a* abutting the collar 809. Thus, the collar 809 is held captive in the space located between the inclined stop 808*a* and the latching projection 808*b*, thus locking the outer shield 806 in the needle-containing position over the needle 822.

As described above, once the outer shield 806 moves to the needle-containing position, further movement in either the distal or the proximal direction is substantially limited due to the collar 809 being held captive in the space located between the inclined stop 808*a* and the latching projection 808*b* of the shield 806. However, it should be understood that use of these components for limiting movement of the outer shield 806 in this manner is merely exemplary, and alternative components could be substituted. For example, the limit ring 500 and tether 520, as described in connection with the third embodiment above, could be utilized in this fifth embodiment as substitute components for accomplishing the same function of substantially limiting movement of the outer shield 806 once it has reached the needle-containing position. That is, the ring 500 of the third embodiment could be disposed over the shield 806 of this fifth embodiment and connected to the syringe barrel 814 by the tether 520 in a manner similar to that described under the third embodiment. Likewise, the limit ring 500 and tether 520, as described in connection with the third embodiment above, could be utilized in the second embodiment as substitute components for the upstanding collar 309, and the rearward extending arm 307, the inclined stop 308a and the downwardly deflectable latching projection 308b, to limit movement of the shield 306 past the needle-containing position.

Likewise, under the third embodiment described above, the limit ring 500 and tether 52 are utilized for substantially limiting movement of the outer shield 431 once it has reached the needle-containing position. It should be understood that these components are merely exemplary and alternative components could be utilized for accomplishing this function. For example, this function could be accomplished in the third embodiment utilizing components employed in the second and fifth embodiments, i.e., the collar 809 disposed on the syringe barrel 814 being held captive in the space located between the inclined stop 808a and the latching projection 808b of the shield 806.

Referring now in detail to the various figures of the drawings wherein like reference characters refer to like parts, there is shown at 900 in FIGS. 54 through 61 a sixth embodiment safety syringe assembly that includes a syringe barrel 914 that is substantially transparent and includes volume measuring indicia 916 on the surface thereof to enable a user to determine the volume of fluid within the barrel 914. The syringe assembly 900 also includes a plunger 918, and a hypodermic needle 922 having a needle tip 926. The syringe assembly 900 includes a needle protector cap 924 (FIG. 56) arranged to snap onto the distal end 931 of the safety syringe assembly 900 to protect the needle prior to use. The deployable outer shield 930 is arranged to move in response to thumb actuation from this retracted position, for example as shown in FIG. 57, to a needle-containing position (best shown in FIG. 61).

Figure 56:
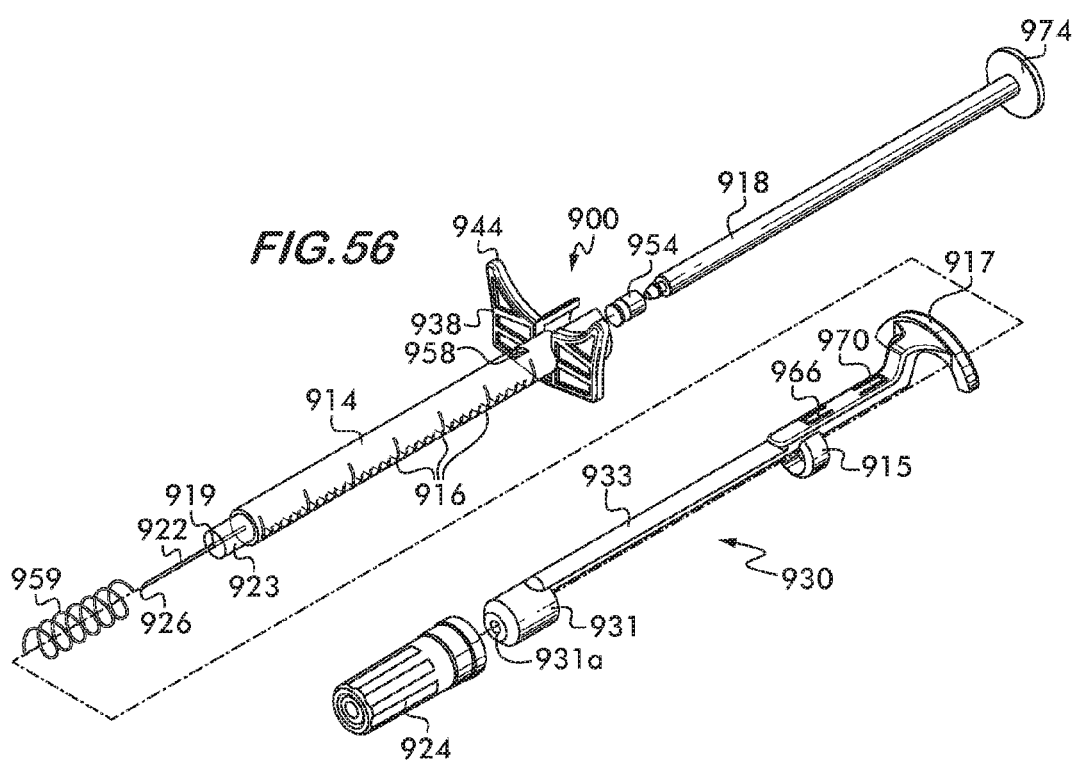
FIG. 56 is an exploded perspective view of the sixth embodiment of the present invention illustrating the components of this embodiment.

As best shown in FIG. 56, the syringe barrel 914 includes a forward end nozzle 923 having a reduced diameter, an axial opening 919 in which the needle 922 is mounted, and a central reservoir 932 (FIG. 59) within which a fluid, e.g., a medicament, may be contained. The needle 922 or needle cannula (those terms being used interchangeably herein) includes a forward tip 926 and is in fluid communication with the reservoir 932 through the reduced diameter nozzle 923. As best shown in FIGS. 56, 57 and 60, an upper catch 958 is located on the top side of the syringe barrel 914 and includes an inclined surface that faces towards the syringe barrel proximal end.

As shown in FIGS. 57 and 60, a compression spring 959 is shown in a compressed state between the front end of the syringe barrel 914 and the outer shield 930 when the outer shield is in the retracted position. The compression spring 959 is sized in diameter to fit over a reduced diameter nozzle 923 located at the distal end of the syringe barrel 914.

As best seen in FIGS. 54 through 56, the syringe barrel 914 includes an outwardly extending flange 938 located towards the proximal end of the barrel 914 which facilitates gripping of the barrel 914 with the user's fingers 942 (shown in phantom in FIGS. 57 and 60) when it is desired to move the plunger 918 relative to the barrel 914 linearly for normal use, such as when moving the plunger 918 through an injection stroke to inject a fluid, e.g., a medicament into a patient. In FIG. 57, the plunger 918 is illustrated as positioned at the terminal end of the central reservoir 932 of the syringe barrel 914. When in this terminus position, either the syringe assembly 900 is ready for loading of a medicament within the syringe barrel 914, also known as the ready position, or the plunger 918 has completed its travel through the injection stroke to deliver a medicament from the central reservoir 932 through the needle 922, and into a patient. As best illustrated in FIG. 59, when it is desired to load a medicament into the syringe barrel 914, such as from a vial, the plunger 918 may be withdrawn from the terminus position in a loading direction as indicated by arrow 921. As illustrated in FIG. 59, during loading of the medicament into the syringe barrel 914, the plunger 918 is pulled back within the central reservoir 932 so that the actuator 917 is forward of the thumb pad 974.

The finger flange 938 may be annular or oblong. Optionally, the finger flange 938 may be provided with upstanding ears 944. Together, the finger flange 938 and the upstanding ears 944 enable the user to position and retain the barrel 914 within fingers 942 (FIG. 57) while using the thumb 977 to move the plunger 918 through the injection stroke. As best shown in FIGS. 55, 57, and 59, the syringe barrel 914 includes a cylindrical wall 946 that extends rearward from the finger flange 938 and is somewhat larger in diameter than the forward portion of the syringe barrel 914.

The plunger 918 extends within the open rear end of the syringe barrel 914 and includes a first end with a stopper 954 positioned within the reservoir of the syringe barrel 914. The stopper 954 is preferably substantially non-compressible. A second end of the plunger 918 extending out of the open rear end of the syringe barrel 914 includes a thumb pad 974 or thumb press area for receiving delivery pressure from a user's thumb 977 for pressing the plunger into the syringe barrel to deliver the fluid, e.g., medicament.

Referring now to FIGS. 54 through 57, the outer shield 930 is shown arranged disposed over the syringe barrel 914 in the retracted position wherein the distal end 931 of the shield 930 is disposed over the forward end nozzle 923 of the syringe barrel 914. The distal end 931 of the outer shield 930 includes a central opening 931a to enable passage of the needle 922 therethrough when the outer shield is in the retracted position. The outer shield also includes a ring 915 arranged to surround the syringe barrel 914 and retain the outer shield 930 thereover. The outer shield 930 is provided with an elongated section 933 that is disposed over a portion of the syringe barrel 914 and is situated opposite the volume measuring indicia 916 so as to not interfere with a user reading said indicia 916. The outer shield 930 also includes an arcuate shaped actuator 917 disposed at the proximal end thereof. Referring again to FIGS. 56, 57 and 60, the upper catch 958 located on the top side of the syringe barrel 914 is arranged for engaging a distally extending deflectable member 966 and a proximally extending deflectable member 970, both members being resiliently deflectable and integral with the deployable outer shield 930.

Referring now to FIG. 57, the plunger 918 is illustrated as having reached the terminus of the injection stroke which is a position that is slightly forward of the position of the actuator 917. Thereafter, if it is desired to deploy the outer shield 930 to the extended needle-containing position, the thumb 977 may be repositioned from the thumb pad 974 to the actuation member 917 of the shield 930. Due to the arcuate shape of the actuation member 917 and the close proximity between the thumb pad 974 and the actuation member 917, movement of the thumb 977 from the thumb pad 974 to the actuation member 917 is an easy transition. For example, the thumb 977 may be easily rolled from the thumb pad 974 to the actuation member 917. Also, this proximity between the thumb pad 974 and the actuation member 917 eliminates the need for the user to reposition fingers 942 on the finger flange 938 or on any other part of the embodiment 900 during this transition, thus enabling the user to maintain the syringe barrel 914 in a relatively safe position during this transition to avoid accidental needle tip pricks.

As thumb pressure is applied to the arcuate actuation member 917 to move the actuation member 917 forward, the forward extending deflectable member 966 deflects upwardly as its rounded forward surface rides up and eventually clears the top surface of the upper catch 958. As the forward extending deflectable member 966 clears the top surface of the upper catch 958, the compressed spring 959 moves from its compressed state towards its uncompressed position, and propels the outer shield 930 to move from its retracted position to its deployed needle-containing position. As best shown in FIG. 61, as the shield 930 continues to move distally towards the needle-containing position, proximally extending deflectable member 970 rides up and over the catch 958. Once the deflectable tab 970 has cleared the upper catch 958, it serves as a stop to prevent movement of the outer shield in the direction of the retracted position to prevent inadvertent contact with a possibly contaminated needle. Simultaneously, as the actuation member 917 moves distally, it eventually reaches finger flange 938 which stops further movement of the outer shield 930 in the distal direction. It should be understood that under the present embodiment, the compression spring 959 is optional. In other words, the compression spring 959 could be omitted and the outer shield 930 could be moved from its retracted position to its deployed needle-containing position in response to manual actuation, e.g., moving the outer shield 930 by thumb pressure.

As an alternative to deploying the outer shield 930 after the plunger 918 has traveled to its terminus within the central reservoir 932, the thumb may be used to depress the actuator member 917 and the thumb press 974 simultaneously to deploy the outer shield 930 as the plunger 918 approaches its terminus within the reservoir 932. Referring now to FIG. 60, the plunger 918 is shown as approaching the terminus of its injection stroke, with some medicament remaining within the central reservoir 932 of the syringe barrel 914, as indicated at 939. In FIG. 60, the thumb 977 is shown depressing the thumb press 974 and the actuation member 917 at the same time. Further simultaneous depression of these two components will cause the plunger 918 to reach its terminus within the reservoir 932, while causing the spring 959 to propel the outer shield 930 from its retracted position to its needle-containing position, in the manner previously described. In this manner, the operator is provided with freedom-of-choice to decide whether to deploy the shield during the injection of the medicament, or after the injection of medicament has been completed.

While various embodiments have been shown and described, various modifications and substitutions may be made thereto without departing from the spirit and scope of the invention. Accordingly, it is to be understood that the present invention has been described by way of illustrations and not limitation.

The invention claimed is:

1. A safety shield assembly for use with a syringe device having a hollow barrel defining a reservoir within which a medicament may be held, a forward projecting hypodermic needle in fluid communication with the reservoir, the syringe device further including a plunger rod assembly comprising a plunger rod slidable within and partially projecting rearward from an open proximal end of said syringe barrel, said plunger rod selectively moveable within the reservoir along a forward injection stroke, whereby medicament is expelled from the reservoir through the needle, said safety shield assembly comprising:
an outer shield axially moveable relative to said syringe barrel between a retracted position and a needle-containing position, said outer shield including an engagement member that engages a first catch member on said syringe barrel in the retracted position; said outer shield not having an operatively positioned member;
a driving member positioned between said outer shield and said syringe barrel that urges said outer shield to said needle-containing position; said driving member retained in an energized condition when said outer shield is retained in said retracted position; and,
a plunger rod assembly release member wherein continued forward movement of said release member disengages said engagement member from said first catch member, said outer shield moving to said needle-containing position;
wherein
said engagement member comprises a proximally extending hook member which is arranged to extend under said first catch member when engaged therewith;
the proximally extending hook member is a rearwardly extending hook member releasably engaged to a syringe barrel catch member; and the plunger rod assembly release member is a release collar extending from the plunger rod assembly;
the hook member comprises an inclined surface releasably mated to a release collar inclined surface and further includes a first and second ramp having a slot between said ramps, the slot stoppingly mated to a catch surface;
the proximally extending hook member is a pair of opposed hook members releasably engaged to a respective pair of syringe barrel catch members; and
the pair of opposed hook members comprises a first hook member having the first and second ramps and a second hook member which does not.

2. The safety shield assembly of claim 1 additionally comprising a finger flange extending outwardly from said syringe barrel.

3. The safety shield of claim 1 further comprising a distortable stopper connected to the plunger rod.

4. The safety shield assembly of claim 1 wherein said plunger rod assembly release member extends from said plunger rod assembly.

5. The safety shield assembly of claim 1 additionally comprising a second catch member disposed on said syringe barrel distally from said first catch member and arranged to engage said engagement member when said outer shield reaches said needle-containing position.

6. The safety assembly of claim 5 wherein said second catch member is disposed on a finger flange extending outwardly from said syringe barrel.

7. The safety shield of claim 1 wherein said outer shield does not have an operatively positioned member located within about its rearward one half.

8. A safety shield assembly for use with a syringe device having a hollow barrel defining a reservoir within which a medicament may be held, a forward projecting hypodermic needle in fluid communication with the reservoir, the syringe device further including a plunger rod assembly comprising a plunger rod slidable within and partially projecting rearward from an open proximal end of said syringe barrel, said plunger rod selectively moveable within the reservoir along a forward injection stroke, whereby medicament is expelled from the reservoir through the needle, said safety shield assembly comprising:
an outer shield axially moveable relative to said syringe barrel between a retracted position and a needle-containing position, said outer shield including an engagement member that engages a first catch member on said syringe barrel in the retracted position; said outer shield not having an operatively positioned member;

a driving member positioned between said outer shield and said syringe barrel that urges said outer shield to said needle-containing position; said driving member retained in an energized condition when said outer shield is retained in said retracted position; and, the plunger rod assembly comprising a plunger rod assembly release member and a stopper wherein continued forward movement of said release member disengages said engagement member from said first catch member after said stopper distorts against said hollow barrel, said outer shield moving to said needle-containing position;

wherein
said engagement member comprises a proximally extending hook member which is arranged to extend under said first catch member when engaged therewith;

the proximally extending hook member is a rearwardly extending hook member releasably engaged to a syringe barrel catch member; and the plunger rod assembly release member is a release collar extending from the plunger rod assembly;

the hook member comprises an inclined surface releasably mated to a release collar inclined surface and further includes a first and second ramp having a slot between said ramps, the slot stoppingly mated to a catch surface;

the proximally extending hook member is a pair of opposed hook members releasably engaged to a respective pair of syringe barrel catch members; and the pair of opposed hook members comprises a first hook member having the first and second ramps and a second hook member which does not.

9. The safety shield assembly of claim 8 additionally comprising a second catch member disposed on said syringe barrel distally from said first catch member and arranged to engage said engagement member when said outer shield reaches said needle-containing position.

10. The safety assembly of claim 9 wherein said second catch member is disposed on a finger flange extending outwardly from said syringe barrel.

11. The safety shield of claim 8 wherein said outer shield does not have an operatively positioned member located within about its rearward one half.

12. A safety shield assembly for use with a syringe device having a hollow barrel defining a reservoir within which a medicament may be held, a forward projecting hypodermic needle in fluid communication with the reservoir, the syringe device further including a plunger rod assembly comprising a plunger rod slidable within and partially projecting rearward from an open proximal end of said syringe barrel, said plunger rod selectively moveable within the reservoir along a forward injection stroke, whereby medicament is expelled from the reservoir through the needle, said safety shield assembly comprising:

an outer shield axially moveable relative to said syringe barrel between a retracted position and a needle-containing position, said outer shield including an engagement member that engages a first catch member on said syringe barrel in the retracted position; said outer shield not having an operatively positioned member;

a driving member positioned between said outer shield and said syringe barrel that urges said outer shield to said needle-containing position; said driving member retained in an energized condition when said outer shield is retained in said retracted position; and, a plunger rod assembly comprising a plunger rod assembly release member and a stopper wherein continued forward movement of said release member disengages said engagement member from said first catch member after said stopper compresses, said outer shield moving to said needle-containing position wherein
said engagement member comprises a proximally extending hook member which is arranged to extend under said first catch member when engaged therewith;

the proximally extending hook member is a rearwardly extending hook member releasably engaged to a syringe barrel catch member; and the plunger rod assembly release member is a release collar extending from the plunger rod assembly;

the hook member comprises an inclined surface releasably mated to a release collar inclined surface and further includes a first and second ramp having a slot between said ramps, the slot stoppingly mated to a catch surface;

the proximally extending hook member is a pair of opposed hook members releasably engaged to a respective pair of syringe barrel catch members; and the pair of opposed hook members comprises a first hook member having the first and second ramps and a second hook member which does not.

13. The safety shield assembly of claim 12 additionally comprising a second catch member disposed on said syringe barrel distally from said first catch member and arranged to engage said engagement member when said outer shield reaches said needle-containing position.

14. The safety assembly of claim 13 wherein said second catch member is disposed on a finger flange extending outwardly from said syringe barrel.

15. The safety shield of claim 12 wherein said outer shield does not have an operatively positioned member located within about its rearward one half.

* * * * *